(12) United States Patent
De Ridder

(10) Patent No.: US 7,613,520 B2
(45) Date of Patent: Nov. 3, 2009

(54) SPINAL CORD STIMULATION TO TREAT AUDITORY DYSFUNCTION

(75) Inventor: Dirk De Ridder, Zelzate (BE)

(73) Assignee: Advanced Neuromodulation Systems, Inc., Plano, TX (US)

( * ) Notice: Subject to any disclaimer, the term of this patent is extended or adjusted under 35 U.S.C. 154(b) by 679 days.

(21) Appl. No.: 11/254,611

(22) Filed: Oct. 20, 2005

(65) Prior Publication Data

US 2006/0116742 A1   Jun. 1, 2006

Related U.S. Application Data

(60) Provisional application No. 60/620,762, filed on Oct. 21, 2004, provisional application No. 60/631,085, filed on Nov. 24, 2004.

(51) Int. Cl.
*A61N 1/18* (2006.01)
(52) U.S. Cl. ............................................. 607/55
(58) Field of Classification Search .......... 607/1, 607/2, 45, 55–57, 116, 139
See application file for complete search history.

(56) References Cited

U.S. PATENT DOCUMENTS

| | | | |
|---|---|---|---|
| 4,541,432 A | 9/1985 | Molina-Negro et al. | |
| 5,335,657 A | 8/1994 | Terry, Jr. et al. | |
| 5,496,369 A | 3/1996 | Howard, III | |
| 5,676,655 A | 10/1997 | Howard, III et al. | |
| 5,697,975 A | 12/1997 | Howard, III | |
| 5,713,847 A | 2/1998 | Howard, III et al. | |
| 5,735,885 A | 4/1998 | Howard, III et al. | |
| 5,788,656 A | 8/1998 | Mino | |
| 5,938,690 A | 8/1999 | Law et al. | |
| 6,210,321 B1 | 4/2001 | Di Mino et al. | |
| 6,295,472 B1 | 9/2001 | Rubinstein et al. | |
| 6,337,997 B1 | 1/2002 | Rise | |
| 6,456,886 B1 | 9/2002 | Howard, III et al. | |
| 6,529,774 B1 | 3/2003 | Greene | |
| 6,567,696 B2 | 5/2003 | Voznesensky et al. | |
| 6,609,031 B1 | 8/2003 | Law et al. | |
| 6,622,047 B2 | 9/2003 | Barrett et al. | |

(Continued)

FOREIGN PATENT DOCUMENTS

WO    WO-01/08617    2/2001

OTHER PUBLICATIONS

Barbas et al., "Projections from the amygdala to basoventral and mediodorsal prefrontal regions in the rhesus monkey," *J. Comp. Neurol.*, 300(4): 549-71, 1990.

(Continued)

*Primary Examiner*—Angela D Sykes
*Assistant Examiner*—Amanda Patton
(74) *Attorney, Agent, or Firm*—Melissa Acosta; Peter Lando; Christopher S. L. Crawford

(57) ABSTRACT

A system and method for treating auditory dysfunction by somatosensory system stimulation. The system and/or method comprises a probe and a device to stimulate the probe. The probe has a stimulation portion subcutaneously implanted in communication with a predetermined spinal cord site. The stimulation portion of the probe may be implanted externally to the spinal cord, or may be implanted epidurally. The stimulation portion may be a laminotomy, paddle, surgical, or multiple electrode lead. The device to stimulate the probe may also be implanted subcutaneously.

12 Claims, 7 Drawing Sheets

U.S. PATENT DOCUMENTS

| | | | |
|---|---|---|---|
| 6,656,172 | B1 | 12/2003 | Hildeband |
| 6,671,555 | B2 | 12/2003 | Gielen et al. |
| 6,690,974 | B2 | 2/2004 | Archer et al. |
| 6,721,603 | B2 | 4/2004 | Zabara et al. |
| 6,735,475 | B1 | 5/2004 | Whitehurst et al. |
| 6,740,072 | B2 | 5/2004 | Starkweather et al. |
| 6,748,276 | B1 | 6/2004 | Daignault, Jr. et al. |
| 2003/0100932 | A1 | 5/2003 | Ciaff |
| 2003/0135248 | A1 | 7/2003 | Stypulkowski |
| 2005/0043646 | A1 | 2/2005 | Viirre et al. |
| 2005/0070971 | A1 | 3/2005 | Fowler et al. |
| 2005/0143799 | A1 | 6/2005 | Black et al. |
| 2005/0143800 | A1 | 6/2005 | Lando et al. |

OTHER PUBLICATIONS

Barbas et al., "Topographically specific hippocampal projections target functionally distinct prefrontal areas in the rhesus monkey," *Hippocampus*, 5(6): 511-33, 1995.

Beurrier et al., "Subthalamic nucleus neurons switch from single-spike activity to burst-firing mode," *J. Neurosci.*, 19(2): 599-609, 1999.

Bremner, "Structural changes in the brain in depression and relationship to symptom recurrence," *CNS Spectr.*, 7(2): 129-30, 2002.

Brown et al., "Motor cortex stimulation for central and neuropathic pain: current status," *Pain*, 104(3): 431-435, 2003.

Brozoski et al., "Elevated fusiform cell activity in the dorsal cochlear nucleus of chinchillas with psychophysical evidence of tinnitus," *J. Neurosci.*, 22(6): 2383-90, 2002.

Bruehlmeier et al., "How does the human brain deal with a spinal cord injury?" *Eur. J. Neurosci.*, 10(12): 3918-22, 1998.

Brumberg, "Ionic mechanisms underlying repetitive high-frequency burst firing in supragranular cortical neurons," *J. Neurosci.*, 20(13): 4829-4843, 2000.

Caetano et al., "Anatomical MRI study of hippocampus and amygdala in patients with current and remitted major depression," *Psychiatry Res.*, 132(2): 141-147, 2004.

Cazals et al., "Alterations in average spectrum of cochleoneural activity by long-term salicylate treatment in the guinea pig: a plausible index of tinnitus," *J. Neurophysiol.*, 80(4): 2113-20, 1998.

Chiry, Oriana, et al.; Patterns of calcium-binding proteins support parallel and hierarchical organization of human auditory areas; European Journal of Neuroscience, 17:397-410, 2003.

Condes-Lara et al., "Brain somatic representation of phantom and intact limb: a fMRI study case report," *Eur. J. Pain*, 4(3): 239-45, 2000.

Coro et al., "Receptor cell habituation in the A1 auditory receptor of four noctuoid moths," *J. Exp. Biol.*, 201(Pt 20): 2879-2890, 1998.

De Ridder, Dirk, et al.; Magnetic and electrical stimulation of the auditory cortex for intractable tinnitus: J. Neurosurg, 100:560-564, 2004.

DelBello et al., "Magnetic resonance imaging analysis of amygdala and other subcortical brain regions in adolescents with bipolar disorder," *Bipolar Disord.*, 6(1): 43-52, 2004.

Diamond et al., "Preclinical research on stress, memory, and the brain in the development of pharmacotherapy for depression," *Eur. Neuropsychopharmacol.*, 14(Suppl. 5): S491-S495, 2004.

Disney et al., "Neurosteroids mediate habituation and tonic inhibition in the auditory midbrain," *J. Neurophysiol.*, 86(2): 1052-6, 2001.

Doetsch et al., "Short-term plasticity in primary somatosensory cortex of the rat: rapid changes in magnitudes and latencies of neuronal responses following digit denervation," *Exp. Brain Res.*, 112: 505-512, 1996.

Drevets et al., "Functional anatomical correlates of antidepressant drug treatment assessed using PET measures of regional glucose metabolism," *Eur. Neuropsychopharmacol.*, 12(6): 527-44, 2002.

Edeline et al., "Auditory thalamus neurons during sleep: changes in frequency selectivity, threshold, and receptive field size," *J. Neurophysiol.*, 84(2): 934-52, 2000.

Eichhammer, Peter, et al.; Brief Report: Neuronavigated Repetitive Transcranial Magnetic Stimulatin in Patients with Tinnitus: A short Case Series; Biol. Psychiatry, 54:862-865, 2003.

Flor et al., "Phantom-limb pain as a perceptual correlate of cortical reorganization following arm amputation," *Nature*, 375(6531): 482-484, 1995.

Flor, "Cortical reorganisation and chronic pain: implications for rehabilitation," *J. Rehabil. Med.*, (41 Suppl): 66-72, 2003.

Fossati et al., "Neuroplasticity: from MRI to depressive symptoms," *Eur. Neuropsychopharmacol.*, 14 Suppl. 5: S503-510, 2004.

Foxe et al., "Multisensory auditory-somatosensory interactions in early cortical processing revealed by high-density electrical mapping," *Cognitive Brain Research*, 10: 77-83, 2000.

Foxe, John J., et al.; Auditory-Somatosensory Multisensory Processing in Auditory Association Cortex: An fMRI Study; J. Neurophysiol., 88:540-543, 2002.

Fu et al., "Auditory cortical neurons respond to somatosensory stimulation," *J. Neuroscience*, 23(20): 7510-7515, 2003.

Givois et al., "Sensory habituation of auditory receptor neurons: implications for sound localization," *J. Exp. Biol.*, 203 (Pt 17): 2529-37, 2000.

Halbert et al., "Evidence for the optimal management of acute and chronic phantom pain: a systematic review," *Clin. J. Pain*, 18(2): 84-92, 2002.

Haldane et al., "New insights help define the pathophysiology of bipolar affective disorder: neuroimaging and neuropathology findings," *Prog. Neuropsychopharmacol. Biol. Psychiatry*, 28(6): 943-60, 2004.

He et al., "Differential distribution of burst and single-spike responses in auditory thalamus," *J. Neurophysiol.*, 88(4): 2152-6, 2002.

He et al., "Modulatory effect of cortical activation on the lemniscal auditory thalamus of the Guinea pig," *J. Neurophysiol.*, 88(2): 1040-50, 2002.

He, "Modulatory effects of regional cortical activation on the onset responses of the cat medial geniculate neurons," *J. Neurophysiol.*, 77(2): 896-908, 1997.

Hilty et al., "A review of bipolar disorder among adults," *Psychiatr. Serv.*, 50(2): 201-13, 1999.

Howard III, "Tinnitus and Auditory Cortex," *J. Neurosurg.*, 101: 171-172, 2004.

Huang et al., "Theta burst stimulation of the human motor cortex," *Neuron*, 45(2): 201-6, 2005.

Huerta et al., "Low-frequency stimulation at the troughs of theta-oscillation induces long-term depression of previously potentiated CA1 synapses," *J. Neurophysiol.*, 75(2): 877-84, 1996.

Jastreboff et al., "Phantom auditory perception (tinnitus): mechanisms of generation and perception," *Neurosci. Res.*, 8(4): 221-54, 1990.

Javitt et al., "Role of cortical N-methyl-D-aspartate receptors in auditory sensory memory and mismatch negativity generation: implications for schizophrenia," *Proc. Natl. Acad. Sci. USA*, 93(21): 11962-7, 1996.

Joliot et al., "Human oscillatory brain activity near 40 Hz coexists with cognitive temporal binding," *Proc. Natl. Acad. Sci. USA*, 91(24): 11748-51, 1994.

Jones, "The thalamic matrix and thalamocortical synchrony," *Trends in Neuroscience*, 24(10): 595-601, 2001.

Kaas et al., "The reorganization of somatosensory cortex following peripheral nerve damage in adult and developing mammals," *Annu. Rev. Neurosci.*, 6: 325-56, 1983.

Kandel, "Cellular mechanisms of hearing and the biological basis of individuality," *Principles of Neural Science*, 3rd ed. Appleton & Lange Norwalk, Connecticut: 1009-1031, 1991.

Katayama et al., "Motor cortex stimulation for phantom limb pain: comprehensive therapy with spinal cord and thalamic stimulation," *Stereotact. Funct. Neurosurg.*, 77(1-4): 159-62, 2001.

Kepecs et al, "Bursting neurons signal input slope," *J. Neurosci.*, 22(20): 9053-62, 2002.

Knecht et al., "Plasticity of plasticity? Changes in the pattern of perceptual correlates of reorganization after amputation," *Brain*, 121(Pt 4): 717-724, 1998.

Kumar et al, "Deep brain stimulation for intractable pain: a 15-year experience," *Neurosurgery*, 40(4): 736-746, 1997.

Lange et al., "Enlarged amygdala volume and reduced hippocampal volume in young women with major depression," *Psychol. Med.*, 34(6): 1059-64, 2004.

Langguth, Berthold, et al.; NeuroReport—Neuronavigated rTMS in a patient with chronic tinnitus. Effects of 4 weeks treatment; Auditory and Vestibular Systems, 14(7):977-980, 2003.

Laszig, Roland, et al.; Benefits of Bilateral Electrical Stimulation with the Nucleus Cochlear Implant in Adults: 6-Month Postoperative Results; Otology & Neurotology, 25:958-968, 2004.

Lee et al., "Discharge profiles of ventral tegmental area GABA neurons during movement, anesthesia, and the sleep-wake cycle," *J. Neurosci.*, 21(5): 1757-66, 2001.

Leinonen, L., et al.; Functional Properties of Neurons in the Temporo-parietal Association Cortex of Awake Monkey; Exp. Brain Res., 39:203-215, 1980.

Lende et al., "Relief of facial pain after combined removal of precentral and postcentral cortex," *J. Neurogurg.*, 34: 537-543, 1971.

Lenz et al., "Characteristics of the bursting pattern of action potentials that occurs in the thalamus of patients with central pain," *Brain Res.*, 496(1-2): 357-360, 1989.

Lenz, F. A., et al.; Neuronal Activity in the region of the Thalamic Principal Sensory Nucleus (Ventralis Caudalis) in Patients with Pain Following Amputations; Neuroscience, 86(4):1065-1081, 1998.

Lever et al., "Brain-derived neurotrophic factor is released in the dorsal horn by distinctive patterns of afferent fiber stimulation," *J. Neurosci.*, 21(12): 4469-77, 2001.

Levy et al., "Treatment of chronic pain by deep brain stimulation: long term follow-up and review of the literature," *Neurosurgery*, 21(6): 885-893, 1987.

Lisman, "Bursts as a unit of neural information: making unreliable synapses reliable," *Trends Neurosci.*, 20(1): 38-43, 1997.

Lotze et al., "Phantom movements and pain. An fMRI study in upper limb amputees," *Brain*, 124(Pt 11): 2268-2277, 2001.

Massaux et al., "Auditory thalamus bursts in anesthetized and non-anesthetized states: contribution to functional properties," *J. Neurophysiol.*, 91(5): 2117-34, 2004.

Matveev, "Differential short-term synaptic plasticity and transmission of complex spike trains: to depress or to facilitate," *Cerebral Cortex*, 10(11): 1143-1153, 2000.

McCormick et al., "Corticothalamic activation modulates thalamic firing through glutamate "metabotropic" receptors," *Proc. Natl. Acad. Sci. USA*, 89(7): 2774-8, 1992.

McIntyre, Cameron C., et al.; Extracellular Stimulation of Central Neurons: Influence of Stimulus Waveform and Frequency on Neuronal Output; J. Neurophysiol., 88:1592-1604, 2002.

Merzenich et al., "Somatosensory cortical map changes following digit amputation in adult monkeys," *J. Comp. Neurol.*, 224(4): 591-605, 1984.

Miller et al., "Feature selectivity and interneuronal cooperation in the thalamocortical system," *J. Neurosci.*, 21(20): 8136-44, 2001.

Mirz et al., "Positron emission tomography of cortical centers of tinnitus," *Hearing Research*, 134: 133-144, 1999.

Moller et al., "Some forms of tinnitus may involve the extralemniscal auditory pathway," *Laryngoscope*, 102: 1165-1171, 1992.

Moller et al., "The non-classical auditory pathways are involved in hearing in children but not in adults," *Neuroscience Letters*, 319: 41-44, 2002.

Moller, "Similarities between chronic pain and tinnitus," *Am. J. Otol.*, 18: 577-585, 1997.

Mooney et al., "Distinct forms of cholinergic modulation in parallel thalamic sensory pathways," *Proc. Natl. Acad. Sci. USA*, 101(1): 320-4, 2004.

Nguyen et al., "Treatment of deafferentation pain by chronic stimulation of the motor cortex: report of a series of 20 cases," *Acta Neurochir. Suppl.*, 68: 54-60, 1997.

Nikolajsen et al., "Phantom limb pain," *Br. J. Anaesth.*, 87(1): 107-16, 2001.

Norton, "Can ultrasound be used to stimulate nerve tissue?" *Biomedical Engineering Online*, 2: 6, 2003.

Oleskevich et al., "Synaptic transmission in the auditory brainstem of normal and congenitally deaf mice," *J. Physiol.*, 540(Pt 2): 447-55, 2002.

Perez-Reyes, "Molecular physiology of low-voltage-activated t-type calcium channels," *Physiol. Rev.*, 83(1): 117-61, 2003.

Peyron et al., "Functional imaging of brain responses to pain. A review and meta-analysis (2000)," *Neurophysiol. Clin.*, 30(5): 263-88, 2000.

Phillips et al., "Neurobiology of emotion perception I: The neural basis of normal emotion perception," *Biol. Psychiatry*, 54(5): 504-14, 2003.

Phillips et al., "Neurobiology of emotion perception II: Implications for major psychiatric disorders," *Biol. Psychiatry*, 54(5): 515-28, 2003.

Pons et al., "Massive cortical reorganization after sensory deafferentation in adult macaques," *Science*, 252(5014): 1857-1860, 1991.

Ramachandran et al., "The perception of phantom limbs. The D. O. Hebb lecture," *Brain*, 121(Pt 9): 1603-1630, 1998.

Ramachandran, "Behavioral and magnetoencephalographic correlates of plasticity in the adult human brain," *Proc. Natl. Acad. Sci. USA*, 90(22): 10413-20, 1993.

Ramcharan et al., "Cellular mechanisms underlying activity patterns in the monkey thalamus during visual behavior," *J. Neurophysiol.*, 84(4): 1982-7, 2000.

Rauch, "Neuroimaging and neurocircuitry models pertaining to the neurosurgical treatment of psychiatric disorders," *Neurosurg. Clin. N. Am.*, 14(2): 213-23, vii-viii, 2003.

Rinaldi et al., "Spontaneous neuronal hyperactivity in the medial and intralaminar thalamic nuclei of patients with deafferentation pain," *J. Neurosurg.*, 74: 415-421, 1991.

Sander et al., "The human amygdala: an evolved system for relevance detection," *Rev. Neurosci.*, 14(4): 303-16, 2003.

Sanes et al., "Metabotropic glutamate receptor activation modulates sound level processing in the cochlear nucleus," *J. Neurophysiol.*, 80(1): 209-17, 1998.

Schwindt et al, "Mechanisms underlying burst and regular spiking evoked by dendritic depolarization in layer 5 cortical pyramidal neurons," *Neurophysiol.*, 81(3): 1341-54, 1999.

Sherman et al., "Chronic phantom and stump pain among American veterans: results of a survey," *Pain*, 18(1): 83-95, 1984.

Sherman, "A wake-up call from the thalamus," *Nat. Neurosci.*, 4(4): 344-6, 2001.

Shulman, Abraham; A Final Common Pathway for Tinnitus—The Medial Temporal Lobe System; International Tinnitus Journal, 1:115-126, 1995.

Suga et al., "Sharpening of frequency tuning by inhibition in the thalamic auditory nucleus of the mustached bat," *J. Neurophysiol.*, 77(4): 2098-114, 1997.

Tardif et al, "Patterns of calcium-binding proteins in human inferior colliculus: identification of subdivisions and evidence for putative parallel systems," *Neuroscience*, 116: 1111-1121, 2003.

Theuvenet et al., "Responses to median and tibial nerve stimulation in patients with chronic neuropathic pain," *Brain Topogr.*, 11(4): 305-313, 1999.

Tonndorf, "The analogy between tinnitus and pain: a suggestion for a physiological basis of chronic tinnitus," *Hear. Res.*, 28(2-3): 271-275, 1987.

Tsubokawa et al., "Chronic motor cortex stimulation for the treatment of central pain," *Acta Neurochir. Suppl.*, 52: 137-139, 1991.

Tsubokawa et al., "Treatment of thalamic pain by chronic motor cortex stimulation," *Pacing Clin. Electrophysiol.*, 14(1): 131-134, 1991.

Urbain et al., "The switch of subthalamic neurons from an irregular to a bursting pattern does not solely depend on their GABAergic inputs in the anesthetic-free rat," *J. Neurosci.*, 22(19): 8665-8675, 2002.

Velasco et al., "Centromedian-thalamic and hippocampal electrical stimulation for the control of intractable epileptic seizures," *J. Clin. Neurophysiology*, 18(6): 495-513, 2001.

Videbech et al., "Hippocampal volume and depression: a meta-analysis of MRI studies," *Am. J. Psychiatry*, 161(11): 1957-66, 2004.

Vonck et al., "Long-term amygdalohippocampal stimulation for refractory temporal lobe epilepsy," *Ann. Neurol.*, 52: 556-565, 2002.

Vonck et al., "Long-term deep brain stimulation for refractory temporal lobe epilepsy," *Epilepsia*, 46(Suppl. 5): 98-99, 2005.

Wallhausser-Franke et al., "Expression of c-fos in auditory and non-auditory brain regions of the gerbil after manipulations that induce tinnitus," *Experimental Brain Research*, 153: 649-654, 2003.

Wan et al., "Synaptic transmission of chaotic spike trains between primary afferent fiber and spinal dorsal horn neuron in the rat," *Neuroscience*, 125(4): 1051-60, 2004.

Weiss et al., "Rapid functional plasticity of the somatosensory cortex after finger amputation," *Exp. Brain Res.*, 134(2): 199-203, 2000.

Weissman et al., "Cross-national epidemiology of major depression and bipolar disorder," *Jama*, 276(4): 293-9, 1996.

Weisz et al., "Abnormal auditory mismatch response in tinnitus sufferers with high-frequency hearing loss is associated with subjective distress level," *BMC Neurosci.*, 5(1): 8, 2004.

Wu et al., "Contribution of AMPA, NMDA, and GABA(A) receptors to temporal pattern of postsynaptic responses in the inferior colliculus of the rat," *J. Neurosci.*, 24(19): 4625-34, 2004.

Yuste et al., "Development and plasticity of the cerebral cortex: from molecules to maps," *J. Neurobiol.*, 41(1): 1-6, 1999.

Zhang et al., "Fos-like immunoreactivity in auditory and nonauditory brain structures of hamsters previously exposed to intense sound," *Experimental Brain Research*, 153: 655-660, 2003.

SPINAL CORD STIMULATION TO TREAT AUDITORY DYSFUNCTION

RELATED APPLICATIONS

This application claims priority to U.S. Provisional Application Nos. 60/620,762 filed Oct. 21, 2004 and 60/631,085 filed Nov. 24, 2004 each of which is incorporated herein by reference in its entirety.

This application is also related to U.S. Provisional Application Nos. 60/620,847 filed Oct. 21, 2004, 60/631,089 filed Nov. 24, 2004, 60/639,365 filed Dec. 27, 2004, 60/620,827 filed Oct. 21, 2004, 60/631,091 filed Nov. 24, 2004, and 60/620,781 filed Oct. 21, 2004 each of which is incorporated by reference in its entirety.

TECHNICAL FIELD

This invention relates to neuronal tissue stimulation for medical treatment, and more particularly to stimulating neuronal tissue in the spinal cord for treating auditory dysfunction.

BACKGROUND OF THE INVENTION

Hearing clarity is taken for granted by most people; however, temporary periods of altered auditory perception are a normal part of existence. Nearly every individual will experience phantom noises such as "ringing in the ears" during their lifetime as a result of exposure to external and/or internal stimuli. Loud noise (reported by Zhang et al., Wallhausser-Franke et al.), certain pharmaceuticals, stress, and various physical conditions can all cause altered auditory perception, usually on a temporary basis. However, for some individuals with auditory dysfunction, altered auditory perception can be permanent.

Auditory dysfunctions are common. For example, in the United States, the prevalence of tinnitus when the whole population is considered is approximately 3%. This prevalence is only 1% under the age of 45 but increases significantly with age, rising to 9% in the population over 65 years (Adams et al., 1999). This roughly translates to 36 million Americans with tinnitus (Heller 2003). Tinnitus is a noise in the ears, often described as ringing, buzzing, roaring, or clicking. Subjective and objective forms of tinnitus exist, with objective tinnitus often caused by muscle contractions or other internal noise sources in the area proximal to auditory structures. In certain cases, external observers can hear the sound generated by the internal source of objective tinnitus. In subjective forms, tinnitus is audible only to the subject. Tinnitus varies in perceived amplitude, with some subjects reporting barely audible forms and others essentially deaf to external sounds and/or incapacitated by the intensity of the perceived noise.

Because auditory dysfunctions often occurs secondary to a pathological state, initial treatment may focus on finding an underlying cause. A subject presenting with, for example, tinnitus may be asked for information regarding medications, recent or chronic noise exposure, and home and work environment. Common medications such as aspirin are known to cause tinnitus in some patients or in elevated dosages. Stress can be a direct cause of tinnitus and can aggravate existing cases. A thorough physical exam is typically made of a subject with complaints of tinnitus to eliminate pathologies such as hypertension, tumors, and infections. Objective tinnitus may be diagnosed using a stethoscope if the source of the noise can be localized. For example, hypertension or arterial disorders may produce objective tinnitus, as the carotid arteries pass close to the auditory organs in humans, and excessive pressure or arterial blockage may cause detectable noise to both the subject and to an outside observer.

If a treatable underlying cause to the auditory dysfunction is identified, treatment may focus on elimination of the cause. For example, hypertensive patients may see a reduction or elimination of tinnitus once anti-hypertensive therapy begins. However, a significant number of patients have untreatable underlying pathologies or have tinnitus in the absence of any identifiable cause. For these patients, treatments for directly reducing or eliminating auditory dysfunction are desirable.

Tinnitus research is actively pursued in the hope of finding efficacious treatments. Recently published work has utilized drug delivery systems such as the system described in U.S. Pat. No. 5,713,847, which includes a catheter inserted into a patient's auditory cortex or thalamus for microinfusing drugs. U.S. Pat. No. 6,656,172 describes a tinnitus treatment that includes inserting intrathecally a catheter for infusing a drug. Other treatment methods may try to mask the perceived tinnitus noise by generating an audible signal of appropriate frequency. WO 01/08617 describes a system with a vibrating probe placed in proximity to the inner ear.

The use of certain stimulating electrodes to mask tinnitus has been published. U.S. Pat. Nos. 5,735,885 and 5,496,369 describe the placement of an electrode in the primary auditory cortex of a patient. U.S. Pat. Nos. 6,456,886 and 5,697,975 also use an electrode placed the auditory cortex, and further describe placement of an electrode in the medial geniculate body of the thalamus.

BRIEF SUMMARY OF THE INVENTION

The present invention comprises a therapeutic system for treating auditory dysfunction having a surgically implanted device in communication with a spinal cord treatment site. The device can include a distal probe, such as, for example, an electrode assembly or electrical stimulation lead. The proximal end of the probe is coupled to an electrical signal source, which, in turn, is operated to stimulate the predetermined dorsal column treatment site. Later embodiments of the invention stimulate the dorsal column or posterior funiculus, which is located between the posterior median septum and the posterior horn in the spinal column.

Embodiments of the invention can operate with various stimulation parameters. One example of stimulation parameters used to treat auditory dysfunctions, such as, for example, tinnitus, may use an amplitude in the range of about 2 mA to about 100 mA, a frequency in the range of about 3 Hz to about 80 Hz, and a pulse width in the range of about 5 microseconds to about 100 microseconds. However, other parameters are used in other embodiments of the invention, such as, for example, higher and lower frequencies, various current amplitudes, and/or pulse width durations. In another embodiment of the invention, a frequency stimulation parameter of about 80 Hz is used. Burst mode stimulation is used in preferred embodiments of the invention. The burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 2 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. More particularly, the maximum inter-spike interval may be about 5 milliseconds. Those of skill in the art realize that this can vary depending upon the patient and the treatment. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, in the range of about 10 milliseconds to about 300 milliseconds, or any range therebetween. Preferably, the minimum inter-burst interval may be about 20 milliseconds. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

Embodiments of the invention also comprise a method for treating auditory dysfunction. The method includes surgically implanting an electrical stimulation lead such as a laminotomy lead, paddle, surgical, or multiple electrode lead. Following implantation, the proximal end of the lead is attached to a signal generator. The signal generator then generates a signal that stimulates a predetermined spinal cord site. The stimulation of the spinal cord site modulates components of the somatosensory system that in turn modulate components of the auditory system's extralemniscal pathway.

In later embodiments of the invention, the stimulation parameters are varied after implantation to optimize auditory dysfunction treatment. The parameters varied include the implantation site on the spinal cord, signal amplitude, frequency, pulsewidth or pulse shape. Burst mode stimulation is used in certain embodiments of the invention.

Other stimulation devices used in certain embodiments are drug pumps which provide chemical stimulation of a predetermined spinal cord site. Chemical stimulation can be provided by delivery of pharmaceuticals or neuroactive substances that, for example, disrupt, block, stimulate, and/or modulate a predetermined spinal cord site.

Magnetic stimulation of a predetermined spinal cord site for the treatment of auditory dysfunction is used in certain embodiments of the present invention. Magnetic stimulation of a predetermined spinal cord site can be provided by internally implanted probes or by externally applied directed magnetic fields.

Yet further, thermal stimulation can be provided via implanted probes that are regulated to heat and/or cold temperatures. In other embodiments, ultrasound stimulation is used as a stimulation source, either by itself or in combination with another stimulation source. For example, in certain embodiments of the invention, ultrasound is used to stimulate active tissue by propagating ultrasound in the presence of a magnetic field as described by Norton (2003), herein incorporated by reference in its entirety. Combinations of stimulation sources are used in some embodiments of the invention.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

I. Definitions

Figure 1A:
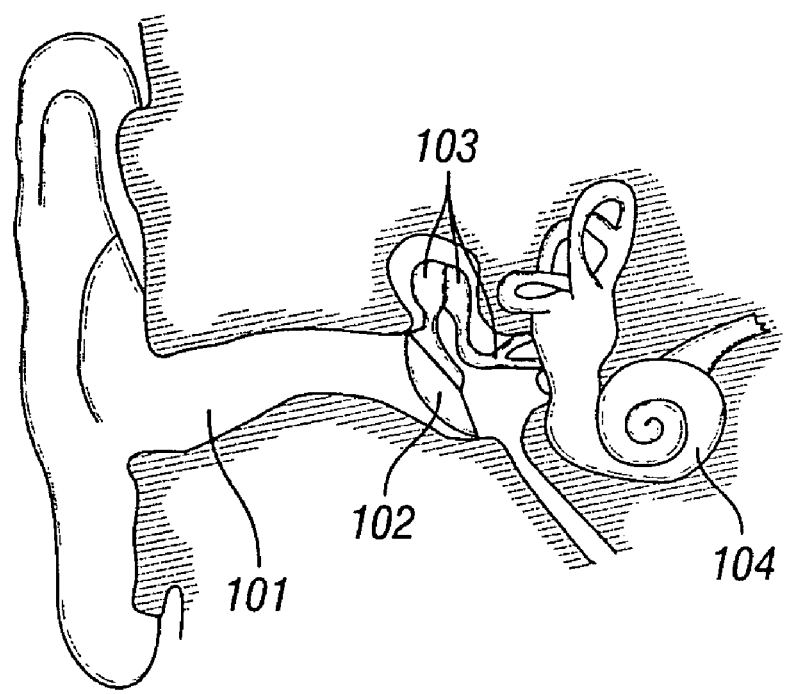
FIGS. 1A-1B are illustrations of the human auditory system including neural connections.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one", but it is also consistent with the meaning of "one or more," "at least one", and "one or more than one". Still further, the terms "having", "including", "containing" and "comprising" are interchangeable and one of skill in the art is cognizant that these terms are open-ended terms.

As used herein, the term "auditory dysfunction" refers to conditions or dysfunctions associated with the auditory pathway. Such auditory dysfunctions can include, but are not limited to tinnitus, hyperacousis, phonophobia, misophonia, auditory agnosia in all its forms, inclusive of verbal and non-verbal auditory agnosia, auditory spatial dysfunction (localizing sound) and auditory hallucinations, inclusive of musical hallucinosis. Auditory hallucinations can occur in schizophrenia or use of certain drugs (e.g., antimuscarinic agents, antiparkinsonian drugs, antidepressants, beta adrenoceptor antagonists and opiates). Auditory dysfunction can also include hearing loss. Hearing loss can be conductive hearing loss (mechanical transmission of sound into the sensory receptors in the cochlea is impaired), sensorineural hearing loss (a loss of function in the sensory receptors in either the cochlea or the auditory nerve), or central hearing loss (a lesion in the brain stem or auditory cortex).

As used herein, the terms "auditory nerve" and "cochlear nerve" are interchangeable and refer to the nerve fibers along which the sensory cells of the ear communicate information to the brain. The auditory or cochlear nerve are part of the vestibulocochlear nerve which carries two kinds of sensation, vestibular (balance) and audition (hearing) from sensory receptors in the inner ear. The auditory nerve consists of the vestibular nerve and the cochlear nerve. The vestibulocochlear nerve is also known as the eighth cranial nerve.

As used herein, the term "in communication" refers to the stimulation lead being adjacent, in the general vicinity, in close proximity, or directly next to or directly on the predetermined stimulation site. Thus, one of skill in the art understands that the lead is "in communication" with the predetermined site if the stimulation results in a modulation of neuronal activity. The predetermined site may be selected from the group consisting of the spinal cord, and the dorsal column of the spinal cord which may include the spinal cord area corresponding to cervical vertebral segments C1 to C8, thoracic vertebral segments T1 to T12, or lumbar vertebral segments L1 and L2. One of ordinary skill in the art will understand that the spinal cord normally terminates at the second lumbar vertebrae L2. However, in certain subjects the spinal cord may terminate before or after the L2 vertebrae segment, and the present invention is intended for use along the entire length of the spinal cord regardless of length.

As used herein, the use of the term "dorsal column" refers to conducting pathways in the spinal cord that are located in the dorsal portion of the spinal cord between the posterior horns, and which comprises afferent somatosensory neurons. The dorsal column is also known as the posterior funiculus.

As used herein, the use of the words "epidural space" or "spinal epidural space" is known to one with skill in the art, and refers to an area in the interval between the dural sheath and the wall of the spinal canal.

As used herein the term "modulate" refers to the ability to regulate positively or negatively neuronal activity. Thus, the term modulate can be used to refer to an increase, decrease, masking, altering, overriding or restoring of neuronal activity.

As used herein, the term "burst firing" or "burst mode" or "burst mode stimulation" refers to an action potential that is a burst of high frequency spikes (300-1000 Hz) (Beurrier et al., 1999). Burst firing acts in a non-linear fashion with a summation effect of each spike. One skilled in the art is also aware that burst firing can also be referred to as phasic firing, rhythmic firing (Lee 2001), pulse train firing, oscillatory firing and spike train firing, all of these terms used herein are interchangeable.

As used herein, the term "tonic firing" or "tonic mode" refers to an action potential that occurs in a linear fashion.

As used herein, the term "burst" refers to a period in a spike train that has a much higher discharge rate than surrounding periods in the spike train (N. Urbain et al., 2002). Thus, burst can refer to a plurality of groups of spike pulses. A burst is a train of action potentials that occurs during a 'plateau' or 'active phase', followed by a period of relative quiescence called the 'silent phase' (Nunemaker, Cellscience Reviews Vol 2 No. 1, 2005.) Thus, a burst comprises spikes having an inter-spike interval in which the spikes are separated by 0.5 milliseconds to about 100 milliseconds. Those of skill in the art realize that the inter-spike interval can be longer or shorter. Yet further, those of skill in the art also realize that the spike rate within the burst does not necessarily occur at a fixed rate; this rate can be variable.

As used herein, the term "spike" refers to an action potential. Yet further, a "burst spike" refers to a spike that is preceded or followed by another spike within a short time interval (Matveev, 2000), in other words, there is an inter-spike interval, in which this interval is generally about 10 ms but can be shorter or longer, for example 5 milliseconds or 0.5 milliseconds.

As used herein, the term "neuronal" refers to a neuron which is a morphologic and functional unit of the brain, spinal column, and peripheral nerves.

As used herein, the term "somatosensory system" refers to the peripheral nervous system division comprising primarily afferent somatic sensory neurons and afferent visceral sensory neurons that receive sensory information from skin and deep tissue, including the 12 cranial and 21 spinal nerves.

As used herein, "spinal cord," "spinal nervous tissue associated with a vertebral segment," "nervous tissue associated with a vertebral segment" or "spinal cord associated with a vertebral segment or level" includes any spinal nervous tissue associated with a vertebral level or segment. Those of skill in the art are aware that the spinal cord and tissue associated therewith are associated with cervical, thoracic and lumbar vertebrae. As used herein, C1 refers to cervical vertebral segment 1, C2 refers to cervical vertebral segment 2, and so on. T1 refers to thoracic vertebral segment 1, T2 refers to thoracic vertebral segment 2, and so on. L1 refers to lumbar vertebral segment 1, L2 refers to lumbar vertebral segment 2, and so on, unless otherwise specifically noted. In certain cases, spinal cord nerve roots leave the bony spine at a vertebral level different from the vertebral segment with which the root is associated. For example, the T11 nerve root leaves the spinal cord myelum at an area located behind vertebral body T8-T9 but leaves the bony spine between T11 and T12.

As used herein, the term "stimulate" or "stimulation" refers to electrical, chemical, and/or magnetic stimulation that modulates the predetermined sites in the brain.

As used herein, the term "treating" and "treatment" refers to modulating certain areas of the brain so that the subject has an improvement in the disease, for example, beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. One of skill in the art realizes that a treatment may improve the disease condition, but may not be a complete cure for the disease.

II. Auditory Pathways

The auditory system comprises components that convert sound pressure waves into neural impulses that are ultimately processed by the nervous system. A simplified version of these components as they appear in humans is shown in FIG. 1B. Auditory canal 101 channels pressure waves to tympanic membrane 102 which moves in response to the incoming waves. Movement of the tympanic membrane 102 is transmitted to three ossicles 103 located in the middle ear. The ossicles 103 amplify the movement of the tympanic membrane 102 so that sound vibrations are converted to high pressure sound waves in fluid located in the cochlea 104. In vivo, the cochlea 104 is coiled like a snail shell.

Figure 1B:
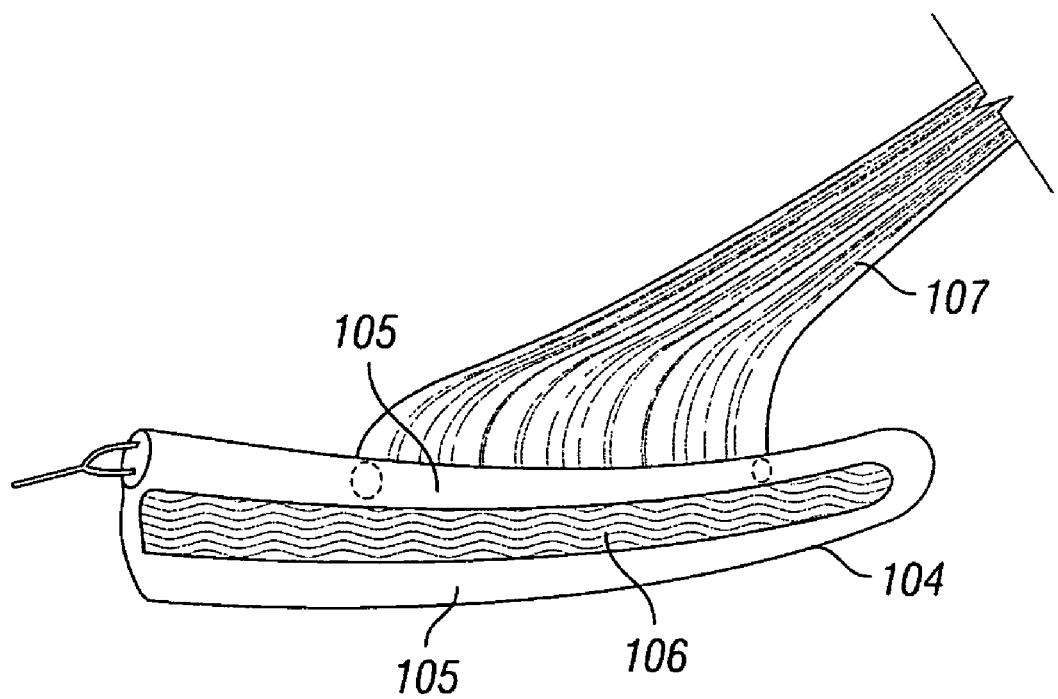

FIG. 1A shows the cochlea 104 of FIG. 1A as it would appear uncoiled. Cochlea 104 is divided into two fluid-filled chambers separated by the organ of Corti 106. Vibrations in the fluid cause mechanical stimulation of sensory receptor cells known as hair cells on the organ of Corti 106. This mechanical stimulation causes ion channels on the hair cells to open, altering their membrane potential and changing the release rate of a synaptic neurotransmitter. Afferent nerve fibers from the auditory nerve 107 take up the neurotransmitter and an action potential in the nerve fibers may be generated depending on the quantity of released neurotransmitter. This is a simplified diagram, and other afferent and efferent nerve fibers are also involved in auditory information collection and processing.

Figure 2:
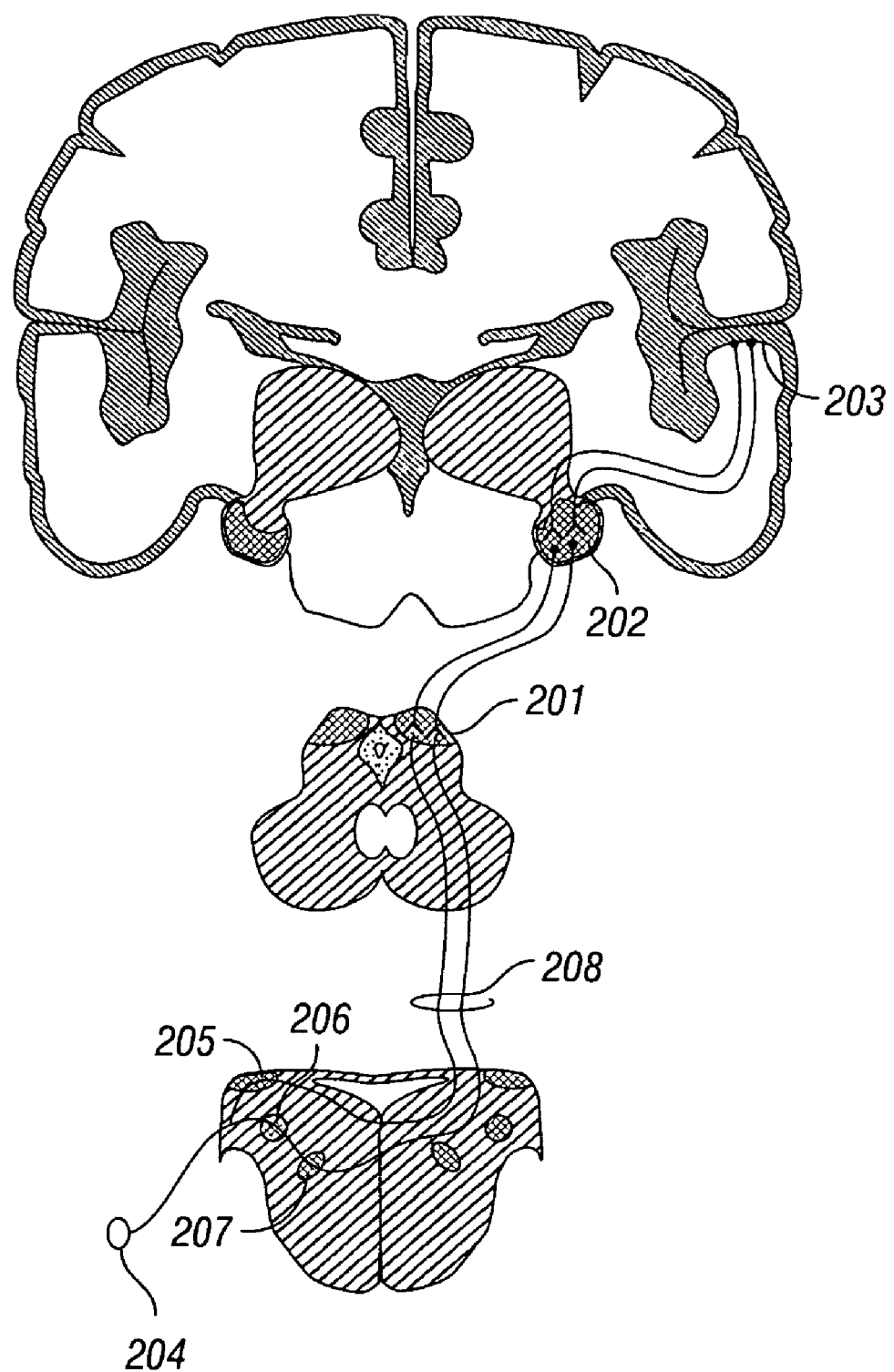
FIG. 2 is an illustration of connections in the lemniscal auditory pathway.

The auditory nerve connects two separate pathways after leaving the cochlea. The lemniscal pathway, also known as the classical or specific auditory pathway, is the route taken for signals that humans consciously perceive as sound information. The lemniscal pathway is phylogenetically the youngest of the two pathways. The lemniscal pathway is organized tonotopically, with specific parts of the pathway carrying information specific to received auditory frequencies. It is also linear, such that the impulse rate of lemniscal neurons is related to the amplitude of sound waves detected at the cochlea. The lemniscal pathway is illustrated in simplified form in FIG. 2. Generally, axons carrying impulses from the cochlea connect to the inferior colliculus 201 and the medial geniculate body 202 in the thalamus to the auditory cortex 203. Specifically, primary axons in synaptic contact with the hair cells of the organ of Corti (106 in FIG. 1A) have their cell bodies in the spiral ganglion 204 and enter the brainstem at the juncture of the pons and cerebellum. Here, each axon bifurcates and synapses in the dorsal and ventral cochlear nuclei 205, 206 of the medulla. Second order axons from the dorsal and ventral cochlear nuclei 205, 206 may synapse in the superior olive 207 or may pass directly to the nucleus of the inferior colliculus 201 via the lateral lemniscus 208. These connections may be made both ipsilaterally (not shown) and contralaterally.

The second pathway connected to by the auditory nerve is the extralemniscal pathway. This pathway is also known as the nonclassical, nonspecific, polysensory, or diffuse auditory pathway, and it produces autonomous reactions to auditory stimuli. Moller and Rollins have found evidence suggesting that this pathway may also be used for conscious hearing in children. The extralemniscal pathway is phylogenetically older than the lemniscal system. Because it is used for autonomous reactions, it is a faster transmission pathway. It is also non-tonotopic and non-linear. Cells of the extralemniscal pathway fire in burst mode and have a slow spontaneous firing rate relative to the lemniscal pathway cells. The auditory extralemniscal pathway makes connections with the somatosensory system at the dorsal cochlear nucleus and the inferior colliculus. Extralemniscal connections at the inferior colliculus occur at the external nucleus and the dorsal cortex. These ascending pathways then connect at all divisions of the medial geniculate bodies, the posterior intralaminar complex, and suprageniculate nuclei at the level of the superior colliculus. Afferent spinal cord neurons connect with the extralemniscal pathway at the external nucleus and the dorsal cortex. An afferent spinal cord neuron may be located in the dorsal column. Afferent spinal cord neurons may also connect directly with other auditory neurons such as, for example, those in the cochlear nucleus.

Connections from the somatosensory system to the auditory system have been explored in the past. Information from the different sensory modalities (sight, hearing, touch, etc.) is known to integrate in most higher organisms, and occurs in the human nervous system. Co-existing cutaneous and auditory responses in neuronal tissue have been observed in the caudomedial auditory cortex, adjacent to the primary auditory cortex (Fu et al., Foxe et al.).

There are also connections between the trigeminal system and the ventral cochlear nucleus. The dorsal cochlear nucleus receives input from the dorsal column (proprioception) nuclei and the ventral cochlear nucleus from the trigeminal ganglion (Shore, Vass et al. 2000; Shore, El Kashlan et al. 2003; Weinberg and Rustioni 1987). The trigeminal ganglion also connects to the superior olivary nucleus (Shore, Vass et al. 2000). Electrical stimulation of the somatosensory trigeminal ganglion can influence the activity of central auditory neurons in a manner distinct from acoustic stimulation, suggesting activation of non-classical auditory pathways (El-Kashlan and Shore 2004). Furthermore, the activation seems to be predominantly ipsilateral (El-Kashlan and Shore 2004). These connections may be involved in generating or modulating perceptions of phantom sounds which can be modified by manipulations of somatic regions of the head and neck ("somatic tinnitus")(Levine, Abel et al. 2003; Shore, El Kashlan et al. 2003). Also, C2 (occipital and greater auricular nerve) innervates the dorsal cochlear nucleus (Kanold and Young 2001) as well as the rest of the body via the cuneate nucleus of the dorsal column (Itoh, Kamiya et al. 1987; Wright and Ryugo 1996).

Thus, it is envisioned that stimulation of the somatosensory system can treat auditory dysfunction, for example, tinnitus by activation of the extralemniscal auditory connections to the somatosensory system.

III. Electrical Stimulation Devices

Figure 3A:
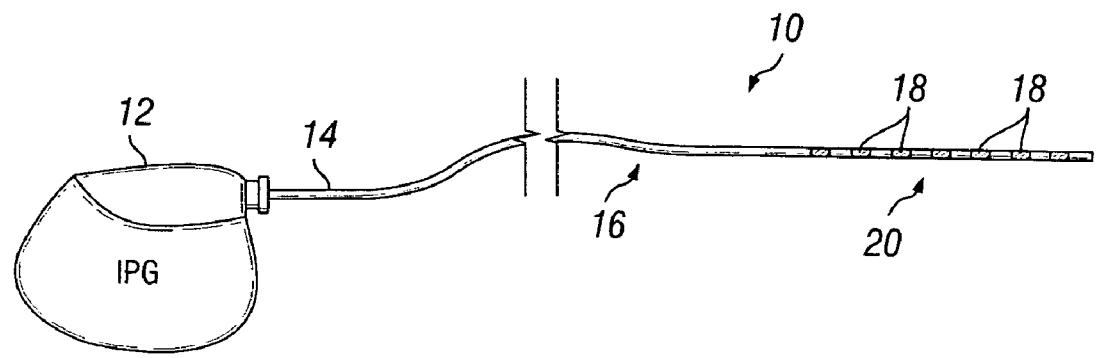
FIGS. 3A-3B illustrate example stimulation systems for electrically stimulating the spinal cord.
Figure 3B:
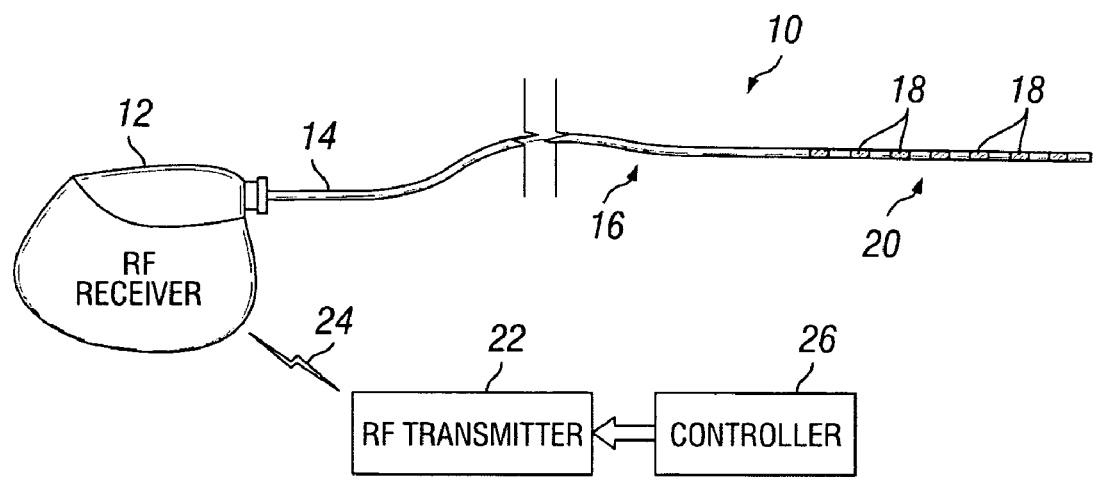

FIGS. 3A-3B illustrate example stimulation systems 10 for electrically stimulating a predetermined site area to treat auditory dysfunction. In general terms, stimulation system 10 includes an implantable electrical stimulation source 12 and one or more implantable electrical stimulation leads 14 for applying electrical stimulation pulses to a predetermined site. In operation, both of these primary components are implanted in a subject's body, as discussed below. In certain embodiments, stimulation source 12 is coupled directly to a connecting portion 16 of stimulation lead 14. In other embodiments, stimulation source 12 is incorporated into the stimulation lead 14 and stimulation source 12 instead is embedded within stimulation lead 14. For example, such a stimulation system 10 may be a Bion® stimulation system manufactured by Advanced Bionics Corporation. Whether stimulation source 12 is coupled directly to or embedded within the stimulation lead 14, stimulation source 12 controls the stimulation pulses transmitted to one or more stimulation electrodes 18 located on a stimulating portion 20 of stimulation lead 14, positioned in communication with a predetermined site, according to suitable stimulation parameters (e.g., duration, amplitude or intensity, frequency, pulse width, etc.). One example of stimulation parameters used to treat auditory dysfunctions such as, for example, tinnitus uses an amplitude in the range of about 2 mA to about 100 mA, a frequency in the range of about 3 Hz to about 80 Hz, and a pulse width in the range of about 5 microseconds to about 100 microseconds. The predetermined site is the spinal cord in this example and may be the dorsal column of the spinal cord in a preferred embodiment. A doctor, the patient, or another user of stimulation source 12 may directly or indirectly input stimulation parameters to specify or modify the nature of the stimulation provided.

Some embodiments employ a burst stimulus. Examples of burst stimulation are found in U.S. application Ser. No. 11/254,465 entitled "New Stimulation Design for Neuromodulation", filed Oct. 20, 2005, and incorporated herein by reference. The burst stimulus comprises a frequency in the range of about 1 Hz to about 300 Hz, more particular, in the range of about 1 Hz to about 12 Hz, and more particularly, in the range of about 1 Hz to about 4 Hz, 4 Hz to about 7 Hz or about 8 Hz to about 12 Hz, 18 Hz to 20 Hz, and 40 Hz. The burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. The interval between spikes can be about 0.5 milliseconds to about 100 milliseconds. The frequency of the spikes within the burst does not need to be constant or regular, in fact, typically, the frequency of the spikes is random or variable. In further embodiments, the burst stimulus is followed by an inter-burst interval. The inter-burst interval has a duration in the range of about 5 milliseconds to about 5 seconds, more preferably, about 10 milliseconds to about 300 milliseconds. It is envisioned that the burst stimulus has a duration in the range of about 10 milliseconds to about 5 seconds, more particularly in the range of about 250 milliseconds to 1 second. The burst stimulus and the inter-burst interval can have a regular pattern or an irregular pattern (e.g., random or irregular harmonics).

In one embodiment, as shown in FIG. 3A, stimulation source 12 includes an implantable pulse generator (IPG). An exemplary IPG is one incorporated in the Genesis® System manufactured by Advanced Neuromodulation Systems, Inc., part numbers 3604, 3608, 3609, and 3644. In another embodiment, as shown in FIG. 3B, stimulation source 12 includes an implantable wireless receiver. An example wireless receiver may be one incorporated in the Renew® System manufactured by Advanced Neuromodulation Systems, Inc., part numbers 3408 and 3416. In another embodiment, the IPG can be optimized for high frequency operation as described in U.S. Provisional Application Ser. No. 60/685,036, filed May 26, 2005, entitled "SYSTEMS AND METHODS FOR USE IN PULSE GENERATION," which is incorporated herein by reference. The wireless receiver is capable of receiving wireless signals from a wireless transmitter 22 located external to the person's body. In some embodiments, the receiver may be stand-alone and no external controller 26 is required. The wireless signals are represented in FIG. 3B by wireless link symbol 24. A doctor, the patient, or another user of stimulation source 12 may use a controller 26 located external to the person's body to provide control signals for operation of stimulation source 12. Controller 26 provides the control signals to wireless transmitter 22, wireless transmitter 22 transmits the control signals and power to the wireless receiver of stimulation source 12, and stimulation source 12 uses the control signals to vary the stimulation parameters of stimulation pulses transmitted through stimulation lead 14 to the predetermined spinal column site. Thus, the external controller 26 can be for example, a handheld programmer, to provide a means for programming the IPG. An example wireless transmitter 122 may be one manufactured by Advanced Neuromodulation Systems, Inc., such as the Renew® System, part numbers 3508 and 3516.

Conventional neuromodulation devices can be modified to apply burst stimulation to nerve tissue of a patient by modifying the software instructions stored in the devices. Specifically, conventional neuromodulation devices typically include a microprocessor and a pulse generation module. The pulse generation module generates the electrical pulses according to a defined pulse width and pulse amplitude and applies the electrical pulses to defined electrodes. The microprocessor controls the operations of the pulse generation module according to software instructions stored in the device.

These conventional neuromodulation devices can be adapted by programming the microprocessor to deliver a number of spikes (relatively short pulse width pulses) that are separated by an appropriate inter-spike interval. Thereafter, the programming of the microprocessor causes the pulse generation module to cease pulse generation operations for an inter-burst interval. The programming of the microprocessor also causes a repetition of the spike generation and cessation of operations for a predetermined number of times. After the predetermined number of repetitions have been completed, the microprocessor can cause burst stimulation to cease for an amount of time (and resume thereafter). Also, in some embodiments, the microprocessor could be programmed to cause the pulse generation module to deliver a hyperpolarizing pulse before the first spike of each group of multiple spikes.

The microprocessor can be programmed to allow the various characteristics of the burst stimulus to be set by a physician to allow the burst stimulus to be optimized for a particular pathology of a patient. For example, the spike amplitude, the inter-spike interval, the inter-burst interval, the number of bursts to be repeated in succession, the amplitude of the hyperpolarizing pulse, and other such characteristics could be controlled using respective parameters accessed by the microprocessor during burst stimulus operations. These parameters could be set to desired values by an external programming device via wireless communication with the implantable neuromodulation device.

In another embodiment, a neuromodulation device can be implemented to apply burst stimulation using a digital signal processor and one or several digital-to-analog converters. The burst stimulus waveform could be defined in memory and applied to the digital-to-analog converter(s) for application through electrodes of the medical lead. The digital signal processor could scale the various portions of the waveform in amplitude and within the time domain (e.g., for the various intervals) according to the various burst parameters.

FIGS. 4A-4I illustrate example stimulation leads 14 that may be used for electrically stimulating a spinal cord site to treat auditory dysfunction. As described above, each of the one or more stimulation leads 14 incorporated in stimulation system 10 includes one or more stimulation electrodes 18 adapted to be positioned in communication with the predetermined site and used to deliver the stimulation pulses received from stimulation source 12. A percutaneous stimulation lead 14, such as example stimulation leads 14a-d, includes one or more circumferential electrodes 18 spaced apart from one another along the length of stimulating portion 20 of stimulation lead 14. Circumferential electrodes 18 emit electrical stimulation energy generally radially (i.e., generally perpendicular to the axis of stimulation lead 14) in all directions. A laminotomy, paddle, or surgical stimulation lead 14, such as example stimulation leads 14e-i, includes one or more directional stimulation electrodes 18 spaced apart from one another along one surface of stimulation lead 14. Directional stimulation electrodes 18 emit electrical stimulation energy in a direction generally perpendicular to the surface of stimulation lead 14 on which they are located. Although various types of stimulation leads 14 are shown as examples, the present invention contemplates stimulation system 10 including any suitable type of stimulation lead 14 in any suitable number. In addition, stimulation leads 14 may be used alone or in combination. For example, medial or unilateral stimulation of the predetermined site may be accomplished using a single electrical stimulation lead 14 implanted in communication with the predetermined site, while bilateral electrical stimulation of the predetermined site may be accomplished using two stimulation leads 14 implanted in communication with the predetermined site on opposite sides of, for example, the spinal cord. Multi-site implantation of stimulation leads can be used. For example, electrodes may be implanted in communication with the dorsal column at the C2 and the T6 level of the spinal cord. Other implantation sites include all other areas of the spinal cord for example any area associated with vertebral segments C1-C8.

In one embodiment, the stimulation source is transcutaneously in communication with the electrical stimulation lead. In "transcutaneous", electrical nerve stimulation (TENS) the stimulation source is external to the patient's body, and may be worn in an appropriate fanny pack or belt, and the electrical stimulation lead is in communication with the stimulation source, either remotely or directly.

In addition to electrical stimulation, other forms of stimulation can be used, for example magnetic. Magnetic stimulation can be provided by internally implanted probes or by externally applied directed magnetic fields, for example, U.S. Pat. Nos. 6,592,509; 6,132,361; 5,752,911; and 6,425,852, each of which is incorporated herein in its entirety. Quick pulses of magnetic stimulation can be applied externally or transcranially, for example repetitive transcranially magnetic stimulation (rTMS).

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

Whether using percutaneous leads, laminotomy leads, or some combination of both, the leads are coupled to one or more conventional neurostimulation devices, or signal generators. The devices can be totally implanted systems and/or radio frequency (RF) systems. An example of an RF system is a MNT/MNR-916CC system manufactured by Advanced Neuromodulation Systems, Inc.

The preferred neurostimulation devices should allow each electrode of each lead to be defined as a positive, a negative, or a neutral polarity. For each electrode combination (e.g., the defined polarity of at least two electrodes having at least one cathode and at least one anode), an electrical signal can have at least a definable amplitude (e.g., voltage), pulse width, and frequency, where these variables may be independently adjusted to finely select the sensory transmitting nerve tissue required to inhibit transmission of neuronal signals. Generally, amplitudes, pulse widths, and frequencies are determinable by the capabilities of the neurostimulation systems, which are known by those of skill in the art. Voltages that may be used can include, for example about 0.5 to about 10 volts, more preferably about 1 to about 10 volts.

It is envisaged that the patient will require intermittent assessment with regard to patterns of stimulation. Different electrodes on the lead can be selected by suitable computer programming, such as that described in U.S. Pat. No. 5,938,690, which is incorporated by reference here in full. Utilizing such a program allows an optimal stimulation pattern to be obtained at minimal voltages. This ensures a longer battery life for the implanted systems.

IV. Implantation of Electrical Devices

Figure 5:
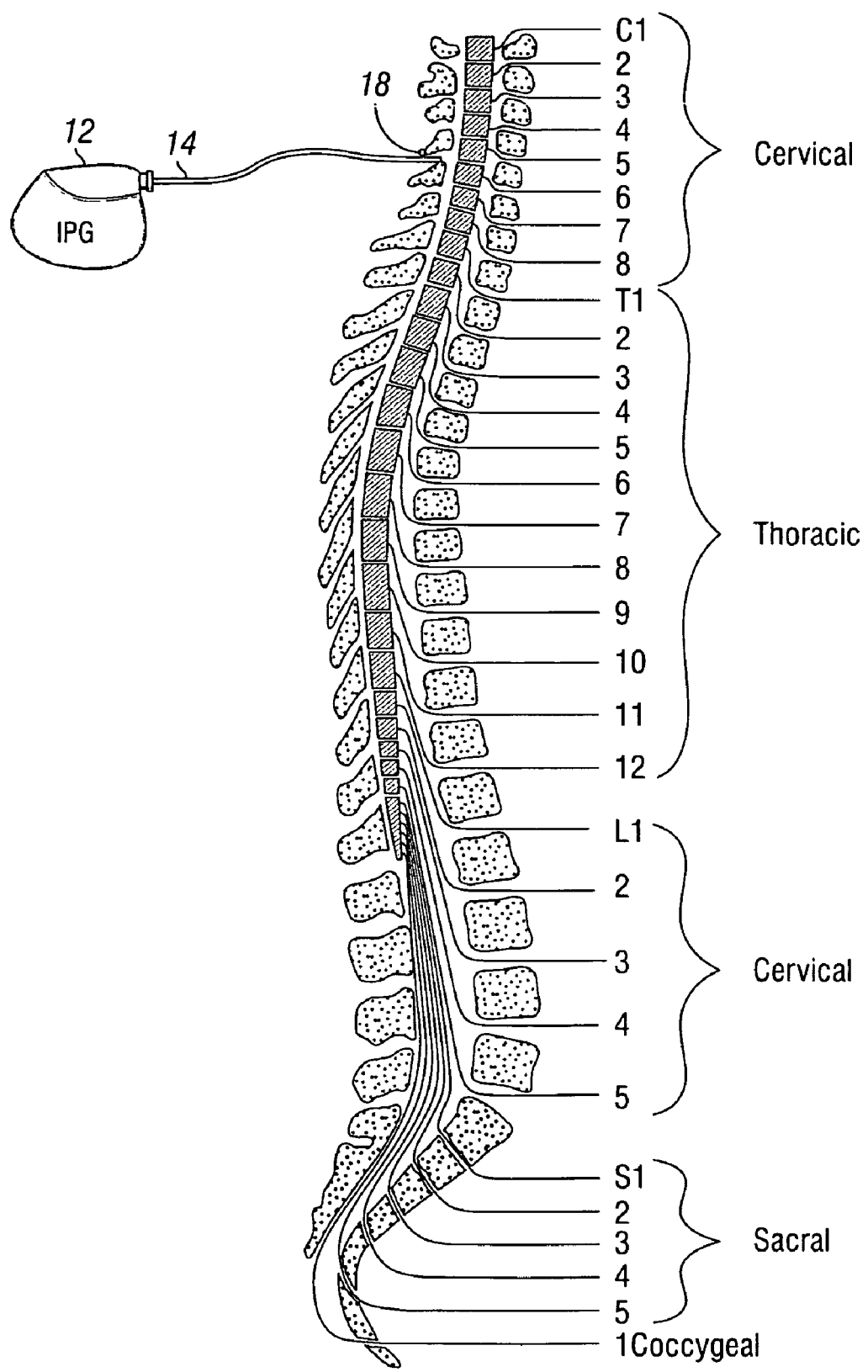
FIG. 5 illustrates implantation of a single stimulation lead.

FIG. 5 illustrates example placement of a single stimulation lead 14 for medial electrical stimulation of the spinal cord by a stimulation electrode 18. For example, electrodes may be implanted in communication with the dorsal column at the C2 and the T6 level of the spinal cord or at any other place in the spinal cord, for example any spiral cord tissue associated with cervical vertebral segments C1-C8. One skilled in the art knows any other area of the dorsal spinal cord can be targeted as well Multiple stimulation leads 14 and electrodes 18 are used in other embodiments of the invention.

Figure 6:
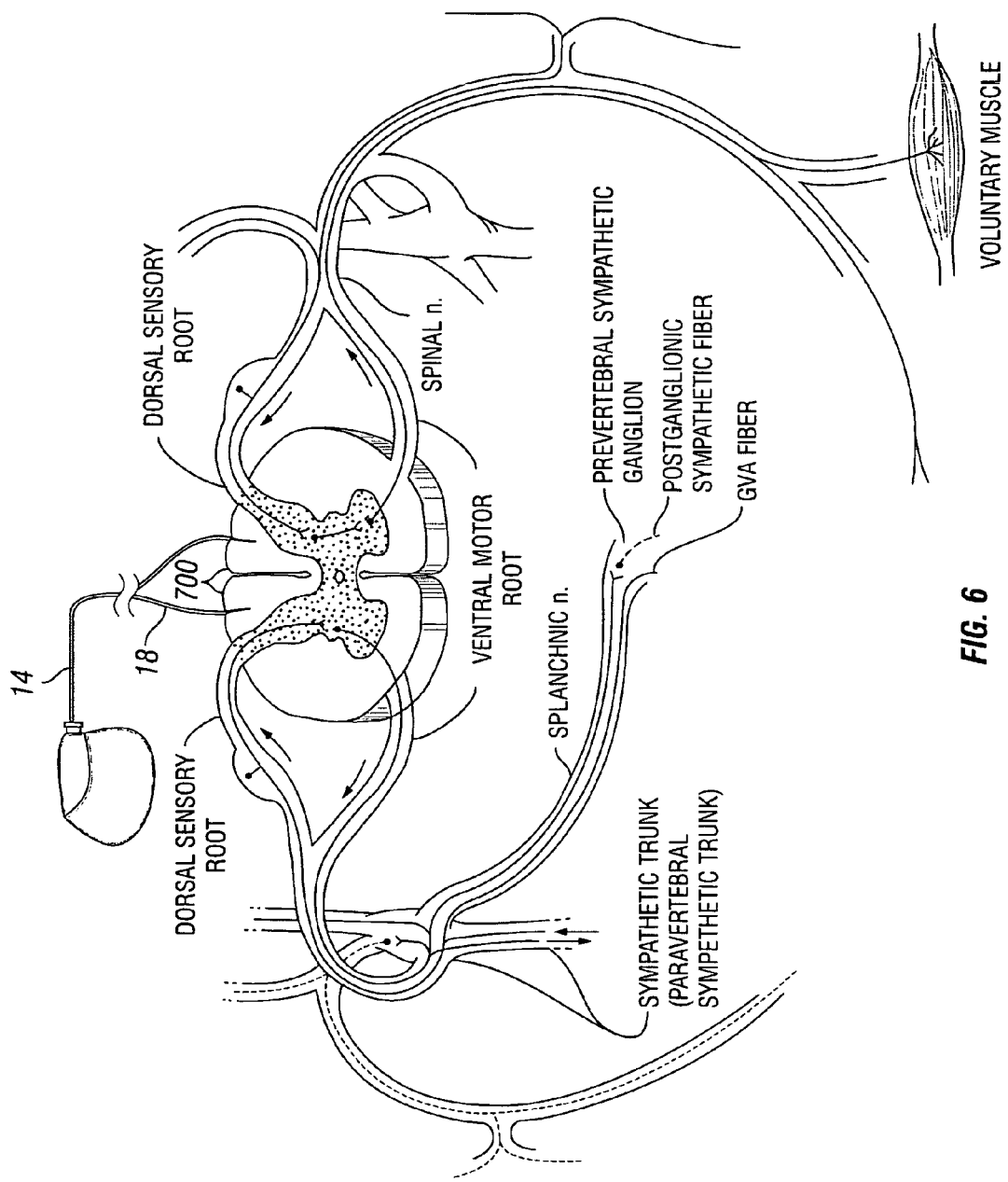
FIG. 6 illustrates an example method of implanting the stimulation system of FIGS. 1A-1B with leads in communication with the dorsal column of the spinal cord.

FIG. 6 is an illustration of an implantable pulse generator with a single simulation lead 14 that is employed with two stimulation electrodes 18 for bilateral stimulation of the dorsal column 700 of the spinal cord. Different numbers of stimulation leads 14 and stimulation electrodes 18 may be used in other embodiments of the invention. Additionally, other portions of the spinal cord may be stimulated by stimulation electrodes 18.

Figure 7:
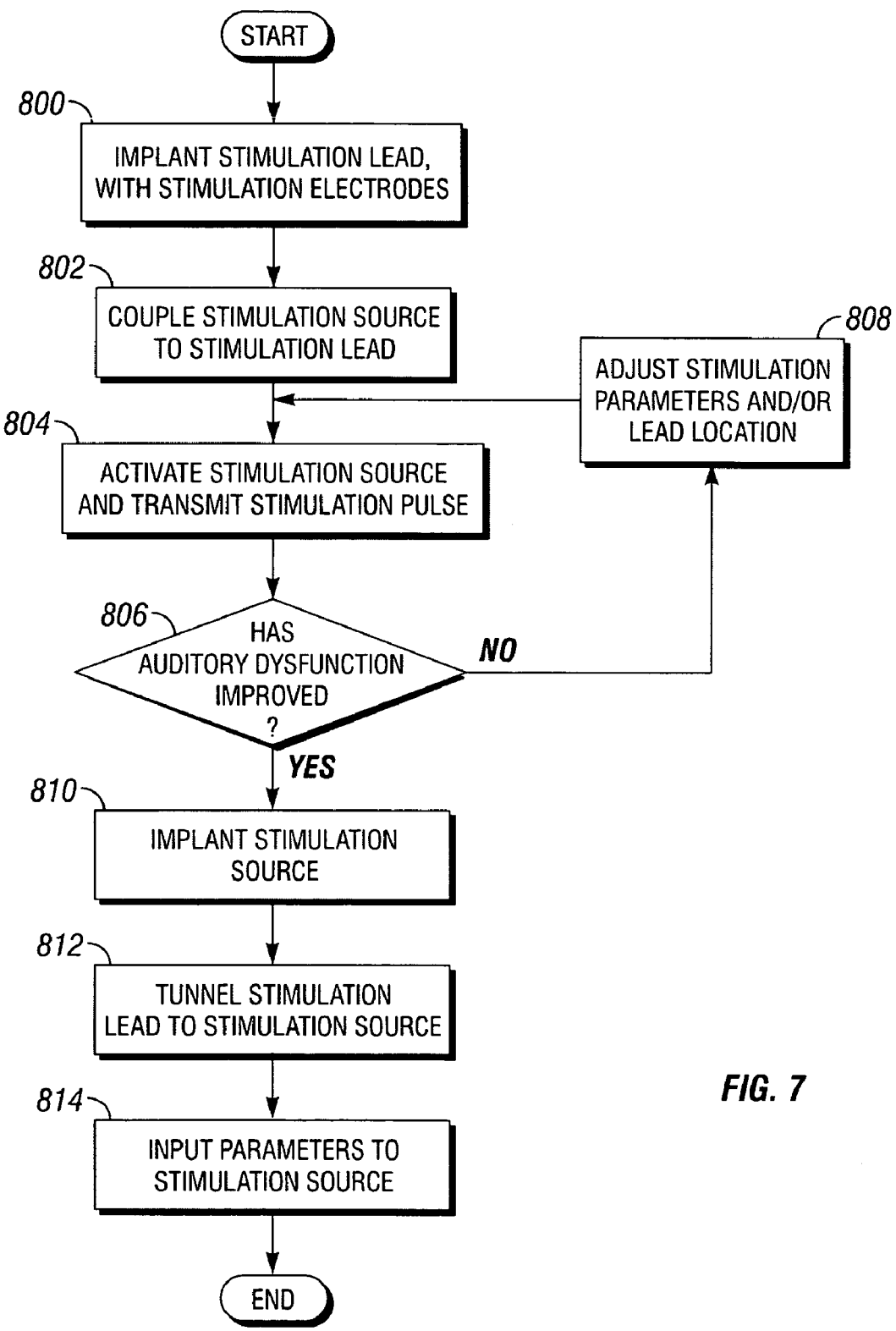
FIG. 7 is a block diagram of steps according to a method for treating auditory dysfunction using a spinal cord stimulation system.

FIG. 7 illustrates an example method of treating auditory dysfunction using stimulation system 10, described above, implanted into a person's body with stimulation lead 14 located in communication with the spinal cord. At step 800, one or more stimulation leads 14 are implanted such that one or more stimulation electrodes 18 of each stimulation lead 14 are positioned in communication with the spinal cord (for the purposes described herein and as those skilled in the art will recognize, when an embedded stimulation system, such as the Bion®, is used, it is positioned similar to positioning the lead 14). Techniques for implanting stimulation leads such as stimulation lead 14 are known to those skilled in the art. In certain embodiments, as described above, one or more stimulation electrodes 18 are positioned in communication with the neuronal tissue of the spinal cord. Stimulation electrodes 18 are commonly positioned external to the dura layer surrounding the spinal cord. Stimulation on the surface of the cord is also contemplated, for example, stimulation may be applied to the spinal cord tissue as well as to the nerve root entry zone. Stimulation electrodes 18 may be positioned in various body tissues and in contact with various tissue layers; for example, subdural, subarachnoid, epidural, and subcutaneous implantation is employed in some embodiments. The electrodes are carried by two primary vehicles: percutaneous leads and a laminotomy lead. Percutaneous leads commonly have two or more, equally-spaced electrodes, which are placed above the dura layer through the use of a Touhy-like needle. For insertion, the Touhy-like needle is passed through the skin, between desired vertebrae, to open above the dura layer. For unilateral auditory dysfunction, percutaneous leads are positioned on the contralateral side of the spinal cord corresponding to the "afflicted" side of the body, and for bilateral auditory dysfunction, a single percutaneous lead is positioned along the patient midline (or two or more leads are positioned on each side of the midline). An example of an eight-electrode percutaneous lead is an OCTRODE® lead manufactured by Advanced Neuromodulation Systems, Inc. A Bion® stimulation system manufactured by Advanced Bionics Corporation is also contemplated. Stimulation of the dorsal column of the spinal cord may be particularly effective in treatment of auditory dysfunction and is used in embodiments of the present invention.

Figure 4A:
FIGS. 4A-4I illustrate example electrical stimulation leads that may be used to electrically stimulate the spinal cord.
Figure 4B:
Figure 4C:
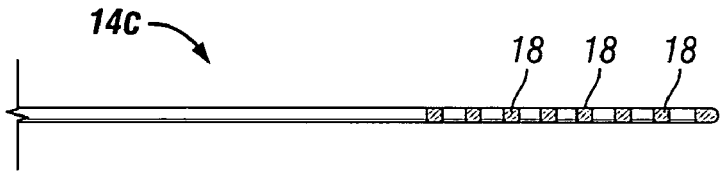
Figure 4D:
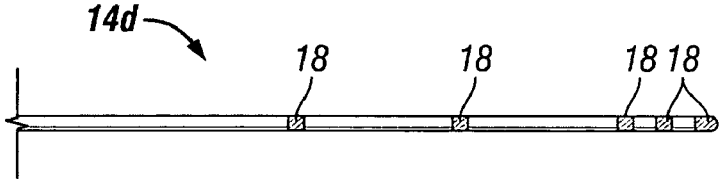
Figure 4E:
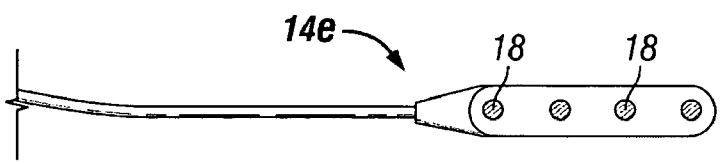
Figure 4F:
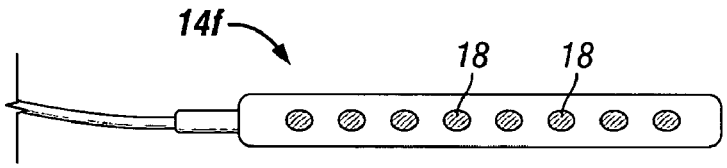
Figure 4G:
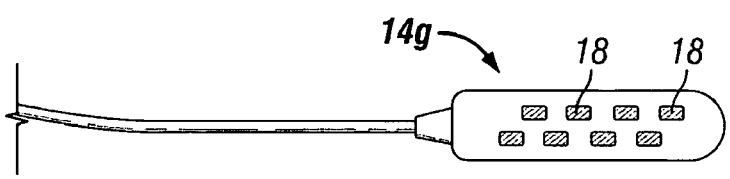
Figure 4H:
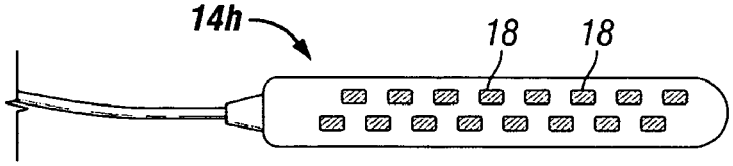
Figure 4I:
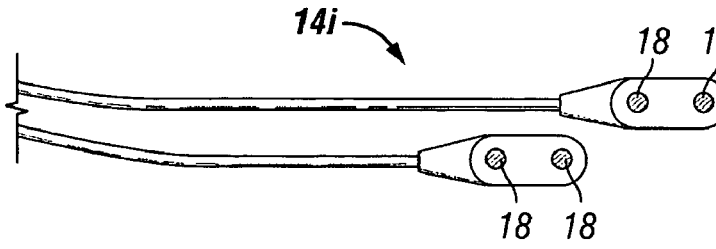

In contrast to the percutaneous leads, laminotomy leads have a paddle configuration and typically possess a plurality of electrodes (for example, two, four, eight, or sixteen) arranged in one or more columns. An example of a sixteen-electrode laminotomy lead is shown in FIG. 4H. Another example of a laminotomy lead is an eight-electrode, two column laminotomy lead called the LAMITRODE® 44, which is manufactured by Advanced Neuromodulation Systems, Inc. Implanted laminotomy leads are commonly transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline. A multi-column laminotomy lead enables reliable positioning of a plurality of electrodes, and in particular, a plurality of electrode columns that do not readily deviate from an initial implantation position.

Laminotomy leads require a surgical procedure for implantation. The surgical procedure, or partial laminectomy, requires the resection and removal of certain vertebral tissue to allow both access to the dura and proper positioning of a laminotomy lead. The laminotomy lead offers a more stable platform, which is further capable of being sutured in place, that tends to migrate less in the operating environment of the human body. Depending on the position of insertion, however, access to the dura may only require a partial removal of the ligamentum flavum at the insertion site. In some embodiments, two or more laminotomy leads may be positioned within the epidural space, and the leads may assume any relative position to one another.

At step 802, if necessary, stimulation source 12 may be coupled directly to connecting portion 16 of stimulation lead 14. Alternatively, as described above and if necessary, stimulation source 12 may not be coupled directly to stimulation lead 14 and may instead be coupled to stimulation lead 14 via an appropriate wireless link. Of course, as those skilled in the art know, an embedded stimulation system will not need to be so coupled.

Intra-implantation trial stimulation may be conducted at steps 804 through 808. These steps may be used to optimize the effect of the treatment on auditory dysfunction. In certain embodiments, the intra-implantation trial stimulation is not performed, and the method proceeds from process 802 to 810. At step 804, stimulation source 12 is activated to generate and transmit stimulation pulses via one or more stimulation electrodes 18. At step 806, informal subjective questioning of the person, formal subjective testing and analysis according to one or more audiology tests and/or other analyses may be performed to determine whether the subject's auditory dysfunction has sufficiently improved through the intra-implantation trial stimulation. If the subject's auditory dysfunction has not sufficiently improved, one or more stimulation parameters may be adjusted, stimulation lead 14 may be moved incrementally or even re-implanted, or both of these modifications may be made at step 808 and the trial stimulation and analysis repeated until the auditory dysfunction has sufficiently improved. Once the stimulation parameters have been properly set and stimulation lead 14 has been properly positioned such that subject's auditory dysfunction has improved, intra-implantation trial stimulation is complete. One of skill in the art is aware that other types of intra-implantation trailing methods or stimulation trails can be used in the present invention, for example, but not limited to transcutaneous electrical nerve stimulation (TENS), transmagnetic stimulation (TMS), nerve blocks, etc.

Once stimulation lead 14 has been properly implanted and secured, and any trial stimulation completed, if necessary, stimulation source 12 is implanted at step 810. Techniques for implanting stimulation sources such as stimulation source 12 are known to those skilled in the art. For non-embedded systems, the implant site is typically a subcutaneous pocket formed to receive and house stimulation source 12. The implant site is usually located some distance away from the insertion site, such as in or near the lower back or buttocks. Where stimulation lead 14 includes connecting portion 16, connecting portion 16 may be tunneled, at least in part, subcutaneously to the implant site of stimulation source 12 at step 812. Some embodiments of the invention may use a non-implantable stimulation source. At step 814, a doctor, the patient, or another user of stimulation source 12 may directly or indirectly input stimulation parameters for controlling the nature of the electrical stimulation provided to the target spinal tissue area, if not already set during any intra-implantation trial stimulation period. Where appropriate, post-implantation trial stimulation may be conducted, over one or more weeks or months for example, and any necessary modifications made accordingly.

Although example steps are illustrated and described, the present invention contemplates two or more steps taking place substantially simultaneously or in a different order. In addition, the present invention contemplates using methods with additional steps, fewer steps, or different steps, so long as the steps remain appropriate for implanting stimulation system 10 into a person for electrical stimulation of the a predetermined site, such as, for example the dorsal column at the C3 level to treat auditory dysfunction.

One technique that offers the ability to affect neuronal function is the delivery of electrical stimulation for neuromodulation directly to target tissues via an implanted device having a probe. The probe can be stimulation lead or electrode. The electrode assembly may be one electrode, multiple electrodes, or an array of electrodes in or around the target area. The proximal end of the probe is coupled to system to operate the device to stimulate the target site. Thus, the probe is coupled to an electrical signal source which, in turn, is operated to stimulate the predetermined treatment site.

V. Infusion Pumps

In further embodiments, it may be desirable to use a drug delivery system independently or in combination with electrical stimulation to result in the stimulation parameters of the present invention. Drug delivery may be used independent of or in combination with a lead/electrode to provide electrical stimulation and chemical stimulation. When used, the drug delivery catheter is implanted such that the proximal end of the catheter is coupled to a pump and a discharge portion for infusing a dosage of a pharmaceutical or drug. Implantation of the catheter can be achieved by combining data from a number of sources including CT, MRI or conventional and/or magnetic resonance angiography into the stereotactic targeting model. Thus, implantation of the catheter can be achieved using similar techniques as discussed above for implantation of electrical leads, which is incorporated herein. The distal portion of the catheter can have multiple orifices to maximize delivery of the pharmaceutical while minimizing mechanical occlusion. The proximal portion of the catheter can be connected directly to a pump or via a metal, plastic, or other hollow connector, to an extending catheter.

Any type of infusion pump can be used in the present invention. For example, "active pumping" devices or so-called peristaltic pumps are described in U.S. Pat. Nos. 4,692,147, 5,840,069, and 6,036,459, which are incorporated herein by reference in their entirety. Peristaltic pumps are used to provide a metered amount of a drug in response to an electronic pulse generated by control circuitry associated within the device. An example of a commercially available peristaltic pump is SynchroMed® implantable pump from Medtronic, Inc., Minneapolis, Minn.

Other pumps that may be used in the present invention include accumulator-type pumps, for example certain external infusion pumps from Minimed, Inc., Northridge, Calif. and Infusaid® implantable pump from Strato/Infusaid, Inc., Norwood, Mass. Passive pumping mechanisms can be used to release an agent in a constant flow or intermittently or in a bolus release. Passive type pumps include, for example, but are not limited to gas-driven pumps described in U.S. Pat. Nos. 3,731,681 and 3,951,147; and drive-spring diaphragm pumps described in U.S. Pat. Nos. 4,772,263, 6,666,845, 6,620,151 all of which are incorporated by reference in their entirety. Pumps of this type are commercially available, for example, Model 3000® from Arrow International, Reading, Pa. and IsoMed® from Medtronic, Inc., Minneapolis, Minn.; AccuRx® pump from Advanced Neuromodulation Systems, Inc., Plano, Tex.

In certain embodiments, the catheter can be in the form of a lead catheter combination, similar to the ones described in U.S. Pat. No. 6,176,242 and U.S. Pat. No. 5,423,877, which are incorporated herein by reference in their entirety.

Still further, the present invention can comprise a chemical stimulation system that comprises a system to control release of neurotransmitters (e.g., glutamate, acetylcholine, norepinephrine, epinephrine), chemicals (e.g., zinc, magnesium, lithium) and/or pharmaceuticals that are known to alter the activity of neuronal tissue. For example, infusion formulation delivery system can utilize a control system having an input-response relationship. A sensor generates a sensor signal representative of a system parameter input (such as levels of neurotransmitters), and provides the sensor signal to a controller. The controller receives the sensor signal and generates commands that are communicated to the infusion formulation delivery device. The infusion formulation delivery device then delivers the infusion formulation output to the predetermined site at a determined rate and amount in order to control the system parameter.

Sensor may comprise a sensor, sensor electrical components for providing power to the sensor and generating the sensor signal, a sensor communication system for carrying the sensor signal to controller, and a sensor housing for enclosing the electrical components and the communication system. Controller may include one or more programmable processors, logic circuits, or other hardware, firmware or software components configured for implementing the control functions described herein, a controller communication system for receiving the sensor signal from the sensor, and a controller housing for enclosing the controller communication system and the one or more programmable processors, logic circuits, or other hardware, firmware or software components. The infusion formulation delivery device may include a suitable infusion pump, infusion pump electrical components for powering and activating the infusion pump, an infusion pump communication system for receiving commands from the controller, and an infusion pump housing for enclosing the infusion pump, infusion pump electrical components, and infusion pump communication system. Such systems are described in U.S. Pat. No. 6,740,072, which is incorporated herein by reference in its entirety.

In certain embodiments, the sensor can be an electrode that senses a hyperactive burst pattern of activity, which in turns stimulates the infusion pump to release a chemical or stimulating drug or agent to modify the neuronal activity. The chemical or stimulating agent can be either an inhibiting agent or stimulating agent.

Herein, stimulating drugs comprise medications, anesthetic agents, synthetic or natural peptides or hormones, neurotransmitters, cytokines and other intracellular and intercellular chemical signals and messengers, other agents such as zinc and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

Similarly, excitatory neurotransmitter agonists (e.g., norepinephrine, epinephrine, glutamate, acetylcholine, serotonin, dopamine), agonists thereof, and agents that act to increase levels of an excitatory neurotransmitter(s) (e.g., edrophonium; Mestinon; trazodone; SSRIs (e.g., fluoxetine, paroxetine, sertraline, citalopram and fluvoxamine); tricyclic antidepressants (e.g., imipramine, amitriptyline, doxepin, desipramine, trimipramine and nortriptyline), monoamine oxidase inhibitors (e.g., phenelzine, tranylcypromine, isocarboxasid)), generally have an excitatory effect on neural tissue, while inhibitory neurotransmitters (e.g., dopamine, glycine, and gamma-aminobutyric acid (GABA)), agonists thereof, and agents that act to increase levels of an inhibitory neurotransmitter(s) generally have an inhibitory effect (e.g., benzodiasepine (e.g., chlordiazepoxide, clonazepam, diazepam, lorazepam, oxazepam, prazepam alprazolam); flurazepam, temazepam, or triazolam). (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g., prazosin, and metoprolol) and agents that decrease levels of excitatory neurotransmitters may inhibit neural activity. Yet further, lithium salts, anesthetics (e.g., lidocane), and magnesium may also be used in combination with electrical stimulation.

VI. Treatment of Auditory Dysfunction

The present method acts to stimulate nerve afferents which in turn stimulate the brain and cause/allow the brain to act in the best interest of the host through use of the brain's natural mechanisms. The prior art fails to recognize that stimulation of a patient's neuronal tissue located in the cervical, thoracic, or lumbar spinal cord region can provide the therapeutic treatments for auditory dysfunction according to the instant invention.

The present invention is particularly useful in the treatment of auditory dysfunction in humans. However, one skilled in the art appreciates that the present invention is applicable to other animals which experience auditory dysfunction. This may include, for example, primates, canines, felines, horses, elephants, dolphins, etc. Utilizing the various embodiments of the present invention, one skilled in the art may be able to modulate the auditory system via spinal cord stimulation to achieve a desirable result.

One technique that offers the ability to affect neuronal function is the delivery of electrical or chemical stimulation for neuromodulation directly to target tissues via an implanted device having a probe. The probe can be stimulation lead or electrode assembly. The electrode assembly may be one electrode, multiple electrodes, or an array of electrodes in or around the target area. The proximal end of the probe is coupled to system to operate the device to stimulate the target site. Thus, the probe is coupled to an electrical signal source, which, in turn, is operated to stimulate the predetermined treatment site.

The predetermined site is the spinal cord at any spinal cord level. For example, the spinal cord can be stimulated at any cervical vertebral level (C1, C2, C3, C4, C5, C6, C7 and C8), thoracic vertebral level (T1, T2, T3, T4, T5, T6, T7, T8, T9, T10, T11, and T12), and/or at the lumbar vertebral level (L1 and L2). Certain embodiments of the invention may preferably stimulate the dorsal column of the spinal cord at any of the above levels Stimulation of the predetermined site is performed to modulate neuronal extralemniscal pathways of the auditory system. Modulation of this neuronal tissue may result in efficacious treatment of auditory dysfunction in a subject. While optimal results from the treatment may result in the complete cessation of auditory dysfunction in a subject, any lessening of the amplitude of a subject's auditory dysfunction may be considered successful according to the present invention.

One example of stimulation parameters that can be used in the present invention is a parameter set with an amplitude in the range of about 2 mA to about 100 mA, a frequency in the range of about 1 Hz to about 80 Hz, and a pulse width in the range of about 5 microseconds to about 100 microseconds.

One of skill in the art is aware that stimulation parameters can be varied to achieve the desired result. One such parameter that may be varied in the present invention is signal frequency. Altering the frequency signal can result in the generation of a bursting type rhythm or burst stimulus frequency or burst mode stimulation, as Burst mode stimulation may also be used as described above and in "New Stimulation Design for Neuromodulation", filed Oct. 20, 2005 incorporated by reference herein.

In certain embodiments, the burst stimulus frequency may be in the range of about 1 Hz to about 100 Hz, more particular, in the range of about 1 Hz to about 12 Hz, and more particularly, in the range of about 1 Hz to about 4 Hz, 4 Hz to about 7 Hz or about 8 Hz to about 12 Hz for each burst. One skilled in the art will further realize that each burst stimulus comprises at least two spikes, for example, each burst stimulus can comprise about 12 to about 100 spikes, more particularly, about 2 to about 10 spikes. Each spike can comprise a frequency in the range of about 50 Hz to about 1000 Hz, more particularly, in the range of about 200 Hz to about 500 Hz. One of skill in the art is aware that the frequency for each spike within a burst can be variable, thus it is not necessary for each spike to contain similar frequencies, e.g., the frequencies can vary in each spike. The inter-spike interval can be also vary, for example, the inter-spike interval, can be about 0.5 milliseconds to about 100 milliseconds or any range therebetween. The burst stimulus can be followed by an inter-burst interval a duration in the range of about 5 milliseconds to about 5 seconds, more preferably, 10 milliseconds to about 300 milliseconds. It is envisioned that the burst stimulus has a duration in the range of about 10 milliseconds to about 5 seconds, more particular, in the range of about 250 msec to 1000 msec (1-4 Hz burst firing), 145 msec to about 250 msec (4-7 Hz), 145 msec to about 80 msec (8-12 Hz) or 1 to 5 seconds in plateau potential firing. The burst stimulus and the inter-burst interval can have a regular pattern or an irregular pattern (e.g., random or irregular harmonics).

In the auditory system, tonic firing transmits the change in the incoming signal which may include the contents of auditory information, while burst firing transmit the valence or importance attached to that sound (Lisman 1997; Sherman 2001; Swadlow and Gusev 2001). Repetitive stimulus presentation results in decreased neuronal response to that stimulus, known as auditory habituation at the single cell level (Ulanovsky et al., 2003), auditory mismatch negativity at multiple cell level (Naatanen et al., 1993; Ulanovsky et al., 2003).

Many auditory dysfunctions are constantly present. For example, tinnitus is usually constantly present, e.g., a non-rational valence is attached to the internally generated sound, and there is no auditory habituation to this specific sound, at this specific frequency. Thus, tinnitus is the result of hyperactivity of lesion-edge frequencies, and auditory mismatch negativity in tinnitus patients is specific for frequencies located at the audiometrically normal lesion edge (Weisz 2004).

As pathological valence of the tinnitus sound is mediated by burst firing, burst firing is increased in tinnitus in the extralemniscal system (Chen and Jastreboff 1995; Eggermont and Kenmochi 1998; Eggermont 2003), in the inner hair cells (Puel 1995; Puel et al., 2002), the auditory nerve (Moller 1984), the dorsal and external inferior colliculus (Chen and Jastreboff 1995), the thalamus (Jeanmonod, Magnin et al., 1996) and the secondary auditory cortex (Eggermont and Kenmochi 1998; Eggermont 2003). Furthermore, quinine, known to generate tinnitus, induces an increased regularity in burst firing, at the level of the auditory cortex, inferior colliculus and frontal cortex (Gopal and Gross 2004). It is contemplated that tinnitus can only become conscious if an increased tonic firing rate is present in the lemniscal system, generating the sound. This increased firing activity has been demonstrated in the lemniscal dorsal cochlear nucleus (Kaltenbach, Godfrey et al., 1998; Zhang and Kaltenbach 1998; Kaltenbach and Afman 2000; Brozoski, Bauer et al., 2002; Zacharek et al., 2002; Kaltenbach et al., 2004), inferior colliculus (Jastreboff and Sasaki 1986; Jastreboff, Brennan et al., 1988; Jastreboff 1990) (Gerken 1996) and primary auditory cortex (Komiya, 2000). Interestingly, not only tonic firing is increased generating the tinnitus sound, but also the burst firing (Ochi and Eggermont 1997) (keeping it conscious) at a regular basis. Repetitive burst firing is known to generate tonic gamma band activity (Gray and Singer 1989; Brumberg, 2000). Thus, it is envisioned that the present invention can be used to modify burst firing, thus modifying tonic gamma activity. However, other pathways may be employed by embodiments of the invention that potentially contribute to the treatment efficacy.

Burst mode firing boosts the gain of neural signaling of important or novel events by enhancing transmitter release and enhancing dendritic depolarization, thereby increasing synaptic potentiation. Conversely, single spiking mode may be used to dampen neuronal signaling and may be associated with habituation to unimportant events (Cooper 2002). It is believed that the main problem in tinnitus is that the internally generated stimulus does not decay due to the presence of regular bursting activity telling the cortex this signal is important and has to remain conscious.

Thus, in the present invention, it is envisioned that a burst mode type stimulation can attack either of these two pathways: slowing down tonic firing in the lemniscal system (below 40 Hz) or removing the valence attached to it by the extralemniscal system by suppressing the regular bursting rhythm, thereby treating auditory dysfunctions such as tinnitus. Yet further, the system of the present invention can also make the auditory dysfunction disappear via auditory habituation. Suppressing the rhythmic burst firing in the frontal cortex may alter the emotional effect of tinnitus, with the tinnitus persisting, but without much influence on the daily life of a tinnitus sufferer.

Thus, using the therapeutic stimulation system of the present invention, the predetermined site is stimulated in an effective amount or effective treatment regimen to decrease, reduce, modulate or abrogate the auditory dysfunction. Thus, a subject is administered a therapeutically effective stimulation so that the subject has an improvement in the parameters relating to auditory dysfunction including the Goebel tinnitus questionnaire or other validated tinnitus questionnaires, audiometry, tinnitus matching, impedence, BAEP, and OAE. The improvement is any observable or measurable improvement. Thus, one of skill in the art realizes that a treatment may improve the patient condition, but may not be a complete cure of the disease.

In certain embodiments, in connection with improvement the electrical stimulation may have a "brightening" effect on the person such that the person looks better, feels better, moves better, thinks better, and otherwise experiences an overall improvement in quality of life.

Treatment regimens may vary as well, and often depend on the health and age of the patient. Obviously, certain types of disease will require more aggressive treatment, while at the same time, certain patients cannot tolerate more taxing regimens. The clinician will be best suited to make such decisions based on the known subject's history.

For purposes of this invention, beneficial or desired clinical results include, but are not limited to, alleviation of symptoms, improvement of symptoms, diminishment of extent of disease, stabilized (i.e., not worsening) state of disease, delay or slowing of disease progression, amelioration or palliation of the disease state, and remission (whether partial or total), whether objective or subjective. The improvement is any observable or measurable improvement. Thus, one of skill in the art realizes that a treatment may improve the patient condition, but may not be a complete cure of the disease.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Treatment of Tinnitus

Thirteen patients with tinnitus were treated by stimulating the dorsal column of the spinal cord indirectly via peripheral nerve stimulation, and one only via direct implantation on the cervical dorsal column. 200 Hz, 250 microsecond pulse width pulses were used with amplitude dependent on an individual threshold. Of the patients stimulated peripherally, four noted a decrease in tinnitus, one noted an increase and eight had no alteration in tinnitus. The one with direct spinal cord stimulation to the dorsal column noted a complete remission in one ear and 0% in the other ear. Tinnitus was evaluated using TMS, TENS, the Goebel tinnitus questionnaire, audiometry, tinnitus matching, impedence, BAEP, and OAE.

Example 2

Treatment of Unilateral Tinnitus

A 39 year old women presented with unilateral left sided narrow band tinnitus since and associated pure tone tinnitus 9 years prior to consultation due to sudden sensorineural hearing loss. The narrow band tinnitus was centered around a pure tone of 3000 Hz and 20 dB above hearing level. It was a compensated grade 3 tinnitus (Goebel and Hiller's tinnitus questionnaire), scoring 7/10 on a VAS. The tinnitus was modified by muscle contractions of the neck. As there were some signs of a somatic modification of the tinnitus a TENS stimulation was applied. With TENS stimulation the pure tone tinnitus was markedly decreased (>80%), with a moderate effect on the white noise component of the tinnitus. A dorsal column stimulator was implanted (lamitrode 44, ANS Medical) extradurally overlying the cervical myelum. For this purpose a midline incision is performed, displacing the neck muscles laterally and performing a C3 laminectomy. A lamitrode 44 is inserted below the lamina of C2 and sutured to the dura at C3. The electrode is connected to an internal pulse generator (Genesis, ANS Medical) via an extension lead. The electrode is activated at 6 Hz 290 pulsewidth at variable amplitudes. Dorsal column stimulation suppressed the pure tone entirely and attenuated the white noise component for 30%.

Example 2

Treatment of Bilateral Tinnitus

A 49 year old man presented with bilateral left sided and right sided tinnitus. The right sided tinnitus is present since 10 years prior to consultation, the left sided tinnitus since 2 years. The right sided tinnitus pitch is at 12000 Hz, 30 dB above hearing threshold, scoring 8/10 on a Visual Analog Scale, the left sided tinnitus is polyphonic, centered around 250 and 8000 Hz, 15 dB above hearing threshold. It is a compensated grade 3 tinnitus (Goebel and Hiller's tinnitus questionnaire). The patient also suffered a deafferentation pain in area C2 and C3 on the right side after a previous rightsided C2-C3 dorsal root rhizotomy. For this deafferentation pain a dorsal column stimulator (lamitrode 44, ANS Medical) was implanted on the area covering the C2-C3 myelum. The dorsal column stimulation suppresses the pain completely and the tinnitus by 80%. Due to a recurrence of both the pain and the tinnitus a revision surgery is performed, suturing the lamitrode 44 into the dura. This again resulted in identical pain and tinnitus suppression.

Thus, electrical stimulation of the somatosensory system is able to treat tinnitus (e.g., somatic or craniocervical tinnitus) by activation of the extralenmiscal auditory connections to the somatosensory system.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Foxe et al., Cognitive Brain Research 10:77-83 (2000)
Fu et al., The Journal of Neuroscience 23(20):7510-7515 (2003)
Jones, Trends in Neuroscience, Vol. 24, No. 10:595-601 (2001)
Moller and Rollins, Neuroscience Letters 319:41-44 (2002)
Moller et al., Laryngoscope 102:1165-1171 (1992)
Mirz et al., Hearing Research 134:133-144 (1999)
Norton, BioMedical Engineering OnLine 2:6 (2003)
Tardif et al., Neuroscience 116:1111-1121 (2003)
Wallhausser-Franke et al., Experimental Brain Research 153: 649-654 (2003)
Zhang et al., Experimental Brain Research 153:655-660 (2003)
U.S. Pat. No. 5,496,369
U.S. Pat. No. 5,697,975
U.S. Pat. No. 5,713,847
U.S. Pat. No. 5,735,885
U.S. Pat. No. 5,788,656
U.S. Pat. No. 6,210,321
U.S. Pat. No. 6,456,886
U.S. Pat. No. 6,656,172
International Pub. No. WO 01/08617

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating auditory dysfunction comprising the steps of:
    implanting at least an electrical lead within a patient such that at least one electrode of the electrical lead is disposed adjacent to the dorsal column of the spinal cord associated with a vertebral segment;
    selecting a plurality of operating parameters for an electrical spinal cord stimulation system that are effective for treating auditory dysfunction;
    programming the electrical spinal cord stimulation system according to the plurality of operating parameters; and
    activating the electrical stimulation system to deliver electrical pulses to the dorsal column of the spinal cord associated with the vertebral segment thereby treating the patient's auditory dysfunction.

2. The method of claim 1 wherein the vertebral segment is a cervical vertebral segment selected from the group consisting of C1, C2, C3, C4, C5, C6, C7, C8, and a combination thereof.

3. The method of claim 1 wherein the electrical stimulation delivers electrical pulses on a substantially continuous basis.

4. The method of claim 1 wherein the plurality of operating parameters include a pulse amplitude parameter, a pulse width parameter, and a pulse frequency parameter.

5. The method of claim 1 wherein the pulse frequency parameter is within the range of about 3 to about 80 Hz.

6. The method of claim 1 wherein the electrical stimulation delivers electrical pulses on a temporary basis in response to receiving an initiation signal from an external control device operated by the patient.

7. The method of claim 1 wherein the selecting comprises:
    temporarily delivering electrical pulses according to the plurality of operating parameters to the dorsal column of the spinal cord associated with the vertebral segment; and
    monitoring the auditory dysfunction while the temporarily delivering is performed.

8. The method of claim 7 wherein the monitoring comprises:
    determining an improvement in the auditory dysfunction.

9. The method of claim 7 wherein the auditory dysfunction is tinnitus, hyperacousis, phonophobia, misophonia, auditory agnosia, auditory spatial dysfunction or auditory hallucinations.

10. The method of claim 1 wherein the lead comprises a plurality of electrodes and the plurality of operating parameters include an electrode configuration.

11. The method of claim 1 further comprising adjusting stimulation parameters to optimize auditory dysfunction treatment.

12. The method of claim 1 wherein the auditory dysfunction is tinnitus.

* * * * *

UNITED STATES PATENT AND TRADEMARK OFFICE
CERTIFICATE OF CORRECTION

PATENT NO. : 7,613,520 B2 Page 1 of 1
APPLICATION NO. : 11/254611
DATED : November 3, 2009
INVENTOR(S) : Dirk De Ridder It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1023 days.

Signed and Sealed this

Nineteenth Day of October, 2010

David J. Kappos
*Director of the United States Patent and Trademark Office*